United States Patent
Payne et al.

(10) Patent No.: US 7,846,160 B2
(45) Date of Patent: Dec. 7, 2010

(54) METHOD AND APPARATUS FOR STERILIZATION

(75) Inventors: F. Mark Payne, Palo Alto, CA (US); Russel M. Sampson, Palo Alto, CA (US)

(73) Assignee: Cytyc Corporation, Marlborough, MA (US)

( * ) Notice: Subject to any disclaimer, the term of this patent is extended or adjusted under 35 U.S.C. 154(b) by 795 days.

(21) Appl. No.: 11/614,900

(22) Filed: Dec. 21, 2006

(65) Prior Publication Data

US 2008/0154256 A1 Jun. 26, 2008

(51) Int. Cl.
*A61B 18/14* (2006.01)

(52) U.S. Cl. ............... 606/45; 606/32; 606/41; 606/49

(58) Field of Classification Search ............. 606/45–46, 606/49
See application file for complete search history.

(56) References Cited

U.S. PATENT DOCUMENTS

| | | | |
|---|---|---|---|
| 552,832 A | 1/1896 | Fort | |
| 725,731 A | 4/1903 | Linn | |
| 1,620,929 A | 3/1927 | Wallerich | |
| 1,827,306 A | 10/1931 | Chapman et al. | |
| 2,190,383 A | 2/1940 | Newman | |
| 2,347,195 A | 4/1944 | Huff | |
| 2,466,042 A | 4/1949 | Reich et al. | |
| 3,228,398 A | 1/1966 | Leonard et al. | |
| 3,324,855 A | 6/1967 | Heimlich | |
| 3,645,265 A | 2/1972 | Majzlin | |
| 3,840,016 A | 10/1974 | Lindemann | |
| 3,845,771 A | 11/1974 | Vise | |
| 3,858,586 A | 1/1975 | Lessen et al. | |
| 3,877,464 A | 4/1975 | Vermes | |
| 3,924,628 A | 12/1975 | Droegemueller et al. | |
| 3,948,270 A | 4/1976 | Hasson | |
| 3,967,625 A | 7/1976 | Yoon | |
| 3,971,378 A | 7/1976 | Krantz | |
| 4,022,215 A | 5/1977 | Benson | |
| 4,057,063 A | 11/1977 | Gieles et al. | |
| 4,082,096 A | 4/1978 | Benson | |
| 4,158,050 A | 6/1979 | Zipper | |
| 4,185,618 A | 1/1980 | Corey | |
| 4,233,025 A | 11/1980 | Larson et al. | |
| 4,359,454 A | 11/1982 | Hoffman | |

(Continued)

FOREIGN PATENT DOCUMENTS

DE 384246 10/1923

(Continued)

OTHER PUBLICATIONS

Adiana options for women—how it works. (Dec. 31, 2005). Retrieved from http://web.archive.org/web/20051124001429/www.adiana.com/products_how.php.*

(Continued)

*Primary Examiner*—Linda C Dvorak
*Assistant Examiner*—Jaymi Della
(74) *Attorney, Agent, or Firm*—Mark A. Vivenzio

(57) ABSTRACT

A medical device and procedure is described for sterilizing a female. A two-part procedure includes an immediate sterilization part and a permanent sterilization part. The immediate sterilization part provides immediate sterility that endures at least until the permanent effects of a tubal occlusion procedure provide permanent sterility.

27 Claims, 18 Drawing Sheets

U.S. PATENT DOCUMENTS

| | | |
|---|---|---|
| 4,380,238 A | 4/1983 | Colucci et al. |
| 4,415,288 A | 11/1983 | Gordon et al. |
| 4,449,528 A | 5/1984 | Auth et al. |
| 4,465,072 A | 8/1984 | Taheri |
| 4,492,231 A | 1/1985 | Auth |
| 4,532,924 A | 8/1985 | Auth et al. |
| 4,568,326 A | 2/1986 | Rangaswamy |
| 4,582,057 A | 4/1986 | Auth et al. |
| 4,601,698 A | 7/1986 | Moulding, Jr. |
| 4,606,336 A | 8/1986 | Zeluff |
| 4,628,924 A | 12/1986 | Cimber |
| 4,662,383 A | 5/1987 | Sogawa et al. |
| 4,676,258 A | 6/1987 | Inokuchi et al. |
| 4,691,703 A | 9/1987 | Auth et al. |
| 4,700,701 A | 10/1987 | Montaldi |
| 4,765,331 A | 8/1988 | Petruzzi et al. |
| 4,788,966 A | 12/1988 | Yoon |
| 4,832,048 A | 5/1989 | Cohen |
| 4,865,047 A | 9/1989 | Chou et al. |
| 4,869,268 A | 9/1989 | Yoon |
| 4,946,440 A | 8/1990 | Hall |
| 4,949,718 A | 8/1990 | Neuwirth et al. |
| 4,955,377 A | 9/1990 | Lennox et al. |
| 4,960,133 A | 10/1990 | Hewson |
| 4,961,435 A | 10/1990 | Kitagawa et al. |
| 4,979,948 A | 12/1990 | Geddes et al. |
| 4,981,465 A | 1/1991 | Ballan et al. |
| 4,983,177 A | 1/1991 | Wolf |
| 5,026,379 A | 6/1991 | Yoon |
| 5,047,028 A | 9/1991 | Qian |
| 5,057,106 A | 10/1991 | Kasevich et al. |
| 5,065,751 A | 11/1991 | Wolf |
| 5,078,717 A | 1/1992 | Parins et al. |
| 5,084,044 A | 1/1992 | Quint |
| 5,105,808 A | 4/1992 | Neuwirth et al. |
| 5,147,353 A | 9/1992 | Everett |
| 5,159,925 A | 11/1992 | Neuwirth et al. |
| 5,186,181 A | 2/1993 | Franconi et al. |
| 5,188,122 A | 2/1993 | Phipps et al. |
| 5,188,602 A | 2/1993 | Nichols |
| 5,217,473 A | 6/1993 | Yoon |
| 5,226,908 A | 7/1993 | Yoon |
| 5,242,437 A | 9/1993 | Everett et al. |
| 5,248,312 A | 9/1993 | Langberg |
| 5,263,585 A | 11/1993 | Lawhon et al. |
| 5,277,201 A | 1/1994 | Stern |
| 5,308,327 A | 5/1994 | Heaven et al. |
| 5,318,532 A | 6/1994 | Frassica |
| 5,322,507 A | 6/1994 | Costello et al. |
| 5,334,193 A | 8/1994 | Nardella |
| 5,334,209 A | 8/1994 | Yoon |
| 5,354,295 A | 10/1994 | Guglielmi et al. |
| 5,364,393 A | 11/1994 | Auth et al. |
| 5,370,649 A | 12/1994 | Gardetto et al. |
| 5,374,261 A | 12/1994 | Yoon |
| 5,374,283 A | 12/1994 | Flick |
| 5,380,317 A | 1/1995 | Everett et al. |
| 5,383,917 A | 1/1995 | Desai et al. |
| 5,395,311 A | 3/1995 | Andrews |
| 5,405,322 A | 4/1995 | Lennox et al. |
| 5,407,071 A | 4/1995 | Lawhon et al. |
| 5,433,708 A | 7/1995 | Nichols et al. |
| 5,437,629 A | 8/1995 | Goldrath |
| 5,443,470 A | 8/1995 | Stern et al. |
| 5,451,204 A | 9/1995 | Yoon |
| 5,474,089 A | 12/1995 | Waynant |
| 5,505,730 A | 4/1996 | Edwards |
| 5,507,743 A | 4/1996 | Edwards et al. |
| 5,514,091 A | 5/1996 | Yoon |
| 5,562,703 A | 10/1996 | Desai |
| 5,562,720 A | 10/1996 | Stern et al. |
| 5,588,961 A | 12/1996 | Leone et al. |
| 5,593,404 A | 1/1997 | Costello et al. |
| 5,609,598 A | 3/1997 | Laufer et al. |
| 5,613,950 A | 3/1997 | Yoon |
| 5,649,924 A | 7/1997 | Everett et al. |
| 5,656,013 A | 8/1997 | Yoon |
| 5,667,520 A | 9/1997 | Bonutti |
| 5,697,882 A | 12/1997 | Eggers et al. |
| 5,702,438 A | 12/1997 | Avitall |
| 5,716,343 A | 2/1998 | Kriesel et al. |
| 5,730,136 A | 3/1998 | Laufer et al. |
| 5,730,725 A | 3/1998 | Yoon |
| 5,769,880 A | 6/1998 | Truckai et al. |
| 5,779,698 A | 7/1998 | Clayman et al. |
| 5,797,903 A | 8/1998 | Swanson et al. |
| 5,800,482 A | 9/1998 | Pomeranz et al. |
| 5,807,389 A | 9/1998 | Gardetto et al. |
| 5,810,847 A | 9/1998 | Laufer et al. |
| 5,827,273 A | 10/1998 | Edwards et al. |
| 5,843,121 A | 12/1998 | Yoon |
| 5,846,238 A | 12/1998 | Jackson et al. |
| 5,871,469 A | 2/1999 | Eggers et al. |
| 5,879,348 A | 3/1999 | Owens et al. |
| 5,885,601 A | 3/1999 | Sokal |
| 5,888,198 A | 3/1999 | Eggers et al. |
| 5,891,134 A | 4/1999 | Goble et al. |
| 5,891,136 A | 4/1999 | McGee et al. |
| 5,897,551 A | 4/1999 | Everett et al. |
| 5,897,553 A | 4/1999 | Mulier et al. |
| 5,935,137 A | 8/1999 | Saadat et al. |
| 5,938,660 A | 8/1999 | Swartz et al. |
| 5,954,715 A | 9/1999 | Harrington et al. |
| 5,954,717 A | 9/1999 | Behl et al. |
| 5,979,446 A | 11/1999 | Loy |
| 6,002,968 A | 12/1999 | Edwards |
| 6,014,589 A | 1/2000 | Farley et al. |
| 6,033,397 A | 3/2000 | Laufer et al. |
| 6,036,687 A | 3/2000 | Laufer et al. |
| 6,041,260 A | 3/2000 | Stern et al. |
| 6,042,596 A | 3/2000 | Bonutti |
| 6,066,139 A * | 5/2000 | Ryan et al. .................. 606/50 |
| 6,068,613 A | 5/2000 | Kriesel et al. |
| 6,068,626 A | 5/2000 | Harrington et al. |
| 6,071,277 A | 6/2000 | Farley et al. |
| 6,077,257 A | 6/2000 | Edwards et al. |
| 6,096,052 A | 8/2000 | Callister et al. |
| 6,117,101 A | 9/2000 | Diederich et al. |
| 6,123,702 A | 9/2000 | Swanson et al. |
| 6,135,997 A | 10/2000 | Laufer et al. |
| 6,139,527 A | 10/2000 | Laufer et al. |
| 6,152,899 A | 11/2000 | Farley et al. |
| 6,159,207 A | 12/2000 | Yoon |
| 6,164,280 A | 12/2000 | Everett et al. |
| 6,165,172 A | 12/2000 | Farley et al. |
| 6,179,832 B1 | 1/2001 | Jones et al. |
| 6,183,468 B1 | 2/2001 | Swanson |
| 6,200,312 B1 | 3/2001 | Zikorus et al. |
| 6,231,496 B1 | 5/2001 | Wilk et al. |
| 6,231,507 B1 | 5/2001 | Zikorus et al. |
| 6,234,178 B1 | 5/2001 | Goble |
| 6,237,606 B1 | 5/2001 | Zikorus et al. |
| 6,238,393 B1 | 5/2001 | Mulier et al. |
| 6,245,065 B1 | 6/2001 | Panescu et al. |
| 6,245,090 B1 | 6/2001 | Gilson et al. |
| 6,254,601 B1 | 7/2001 | Burbank et al. |
| 6,258,084 B1 | 7/2001 | Goldman et al. |
| 6,263,248 B1 | 7/2001 | Farley et al. |
| 6,277,089 B1 | 8/2001 | Yoon |
| 6,293,942 B1 | 9/2001 | Goble et al. |
| 6,296,639 B1 | 10/2001 | Truckai et al. |
| 6,309,384 B1 | 10/2001 | Harrington et al. |
| 6,315,776 B1 | 11/2001 | Edwards et al. |
| 6,322,559 B1 | 11/2001 | Daulton et al. |

| | | | |
|---|---|---|---|
| 6,346,102 B1 | 2/2002 | Harrington et al. | |
| 6,352,549 B1 | 3/2002 | Everett | |
| 6,364,877 B1 | 4/2002 | Goble et al. | |
| 6,369,465 B1 | 4/2002 | Swanson | |
| 6,395,012 B1 | 5/2002 | Yoon et al. | |
| 6,398,780 B1 | 6/2002 | Farley et al. | |
| 6,428,537 B1 | 8/2002 | Swanson | |
| 6,432,116 B1 | 8/2002 | Callister et al. | |
| 6,475,213 B1 | 11/2002 | Whayne et al. | |
| 6,485,500 B1 | 11/2002 | Kokish et al. | |
| 6,508,815 B1 | 1/2003 | Strul et al. | |
| 6,554,780 B1 | 4/2003 | Sampson et al. | |
| 6,663,626 B2 | 12/2003 | Truckai et al. | |
| 6,679,269 B2 | 1/2004 | Swanson | |
| 6,712,810 B2 | 3/2004 | Harrington et al. | |
| 6,712,815 B2 | 3/2004 | Sampson et al. | |
| 6,726,682 B2 | 4/2004 | Harrington et al. | |
| 6,743,184 B2 | 6/2004 | Sampson et al. | |
| 6,764,488 B1 | 7/2004 | Burbank et al. | |
| 6,813,520 B2 | 11/2004 | Truckai et al. | |
| 6,964,274 B1* | 11/2005 | Ryan et al. | 128/830 |
| 2001/0041900 A1 | 11/2001 | Callister et al. | |
| 2002/0022870 A1 | 2/2002 | Truckai et al. | |
| 2002/0029051 A1 | 3/2002 | Callister et al. | |
| 2002/0072499 A1 | 6/2002 | Clagett | |
| 2002/0072745 A1 | 6/2002 | Truckai et al. | |
| 2002/0177846 A1* | 11/2002 | Mulier et al. | 606/27 |
| 2003/0093101 A1 | 5/2003 | O'Heeron et al. | |
| 2003/0130711 A1 | 7/2003 | Pearson | |
| 2003/0199863 A1 | 10/2003 | Swanson | |
| 2004/0054368 A1 | 3/2004 | Truckai et al. | |
| 2004/0118166 A1 | 6/2004 | Huang et al. | |
| 2004/0172051 A1 | 9/2004 | Ravikumar | |
| 2004/0204720 A1 | 10/2004 | Harrington et al. | |
| 2004/0255958 A1 | 12/2004 | Harrington et al. | |
| 2005/0085880 A1 | 4/2005 | Truckai et al. | |
| 2005/0155608 A1 | 7/2005 | Pavcnik et al. | |
| 2005/0217680 A1 | 10/2005 | Callister et al. | |
| 2006/0135956 A1 | 6/2006 | Sampson et al. | |
| 2008/0071269 A1* | 3/2008 | Hilario et al. | 606/50 |

FOREIGN PATENT DOCUMENTS

| | | |
|---|---|---|
| DE | 22 22 820 | 11/1973 |
| DE | 4001086 | 1/1990 |
| EP | 0 056 178 A1 | 4/1981 |
| EP | 0 584 930 A1 | 7/1993 |
| EP | 1 400 182 | 6/2004 |
| EP | 1 568 325 | 8/2005 |
| FR | 774.550 | 9/1934 |
| FR | 70.43012 | 6/1972 |
| JP | 48-67586 | 9/1973 |
| JP | 58-32756 | 2/1983 |
| JP | 63-318934 | 12/1988 |
| WO | WO 92/19145 | 11/1992 |
| WO | WO 94/00178 | 1/1994 |
| WO | WO 94/07445 | 4/1994 |
| WO | WO 94/10948 | 5/1994 |
| WO | WO 94/23794 | 10/1994 |
| WO | WO 95/04385 | 2/1995 |
| WO | WO 95/05869 | 3/1995 |
| WO | WO 95/07664 | 3/1995 |
| WO | WO 95/10326 | 4/1995 |
| WO | WO97/12569 | 4/1997 |
| WO | WO 99/58070 | 11/1999 |
| WO | WO 01/97897 | 12/2001 |

OTHER PUBLICATIONS

International Search Report and Written Opinion from related PCT Application No. PCT/US2007/087864 dated Jul. 30, 2008.

D.E. Haines et al., "Observations on Electrode-Tissue Interface Temperature and Effect on Electrical Impedance During Radiofrequency Ablation of Ventricular Myocardium," *Circulation*, vol. 82, No. 3, Sep. 1990, pp. 1034-1038.

C. Nibley et al., "Prevention of Impedance Rise During Radiofrequency Current Catheter Ablation by Intra-Electrode Tip Chilling," *Circulation* [Abstracts From the 67th Scientific Sessions, Dallas Convention Center, Dallas, Texas, Nov. 14-17, 1994], vol. 90, No. 4, Part 2, Oct. 1994, p. 460.

W.M. Jackman et al., "Radiofrequency Current Directed Across the Mitral Anulus With a Bipolar Epicardial-Endocardial Catheter Electrode Configuration in Dogs," *Circulation*, vol. 78, No. 5, Nov. 1988, pp. 1288-1298.

"Essure: the non-incisional approach to permanent birth control", Patient Information Booklet, © 2004 by Conceptus Incorporated.

"Tubal Ligation—Fimbriectomy: Tubal Reversal is Possible after Fimbriectomy" Datasheet [on-line] Chapel Hill Tubal Reversal Center, 2004 [retrieved on Oct. 19, 2004] Retrieved from the Internet: <URL: http://www.tubal-reversal.net/print/printer-friendly-tubal_ligation_fimbriectomy.htm >.

"Tubal Ligation and Resection: Tubal Ligation by Parkland and Irving Methods" Datasheet [on-line] Chapel Hill Tubal Reversal Center, 2004 [retrieved on Oct. 19, 2004] Retrieved from the Internet: <URL: http://www.tubal-reversal.net/print/printer-friendly-tubal_ligation_resection.htm >.

"Tubal Ligation—Tubal Ring or Clip: Tubal Ligation with Tubal Rings or Tubal Clips" Datasheet [on-line] Chapel Hill Tubal Reversal Center, 2004 [retrieved Oct. 19, 2004] Retrieved from the Internet: <URL: http://www.tubal-reversal.net/tubal_ligation-tubal_ring-tubal_clip.htm >.

"Tubal Ligation—Pomeroy Technique: Pomeroy Tubal Ligation and Resection" Datasheet [on-line] Chapel Hill Tubal Reversal Center, 2004 [retrieved Oct. 19, 2004 ] Retrieved from the Internet: < http://www.tubal-reversal.net/print/printer-friendly-tubal_ligation_Pomeroy.htm >.

"Tubal Ligation Methods: Coagulation Methods of Tubal Ligation" Datasheet [on-line] Chapel Hill Tubal Reversal Center, 2004, [retrieved Oct. 19, 2004] Retrieved from the Internet: < http://www.tubal-reversal.net/tubal_ligation_coagulation.htm >.

"Essure, Permanent Birth Control by Conceptus: What is Essure?" Product Information Sheet [on-line] [retrieved Oct. 19, 2004] Retrieved from the Internet: < URL: http://www.essure.com/consumer/c_what_is_essure.aspx >.

METI-MyriadLase, SteriLase, Powerpoint Presentation, published at least as of Jun. 13, 2006, 6 pp.

* cited by examiner

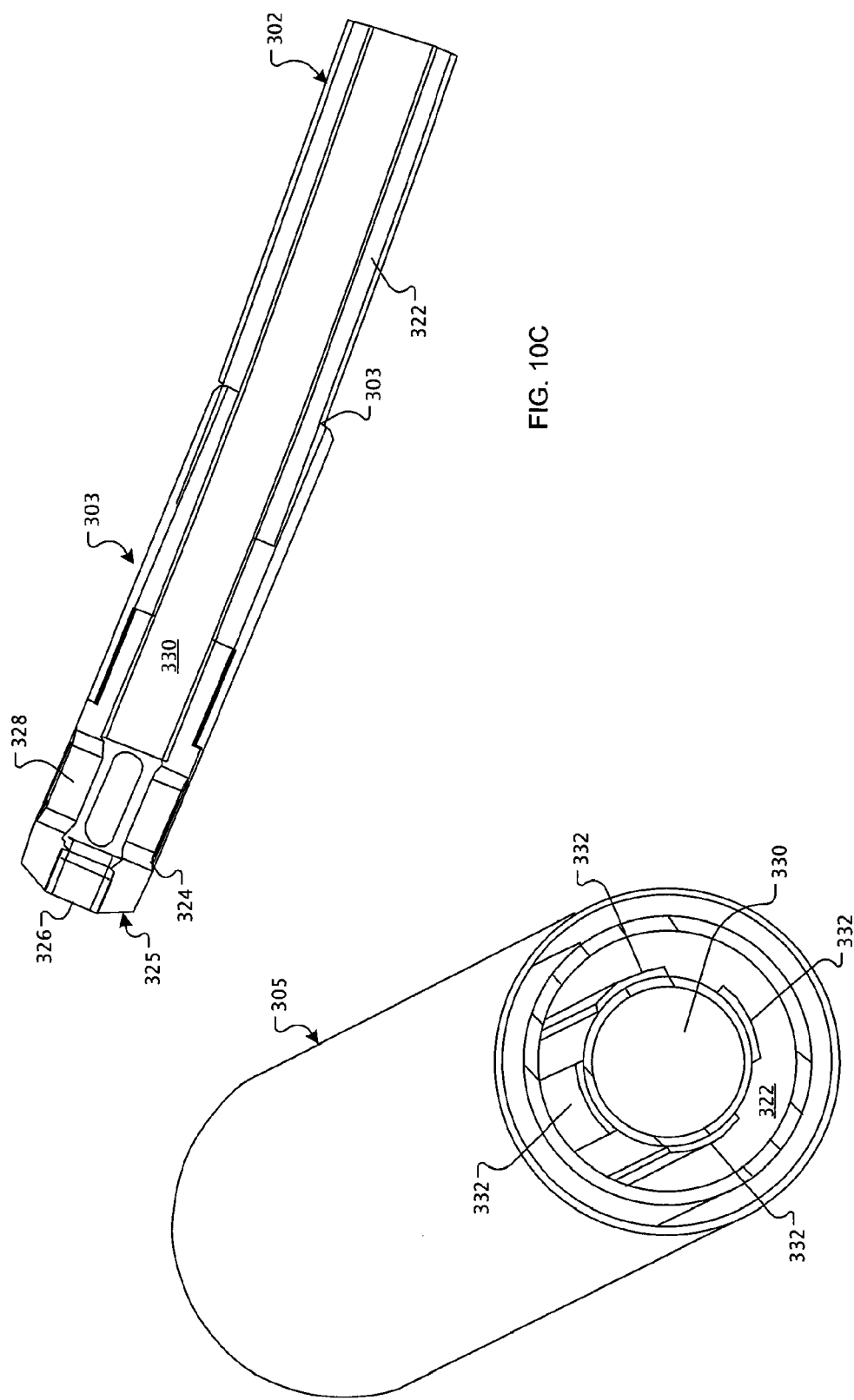

METHOD AND APPARATUS FOR STERILIZATION

TECHNICAL FIELD

This invention relates to a medical device and procedure.

BACKGROUND

Female sterilization typically involves occluding the fallopian tubes to prevent sperm access to an egg within a female's fallopian tube. One conventional female sterilization procedure is laparoscopic tubal occlusion. In this procedure, an incision is made in the abdominal wall to provide access to the fallopian tubes. The tubes are surgically occluded with the aid of a laparoscope, for example, using bipolar or monopolar coagulation. Laparoscopic tubal occlusion is invasive and requires multiple incisions and passing of several instruments and a gaseous distension medium into the patient's abdomen. Thermal and mechanical injury to the surrounding tissues and organs has been reported.

Minimally invasive transcervical approaches to female sterilization have also been used. One such procedure involves placing small, flexible devices into the fallopian tubes; the devices are inserted transcervically into the uterine cavity providing access to the fallopian tubes. The devices are made from polyester fibers and metals and once in place, body tissue grows into the devices and blocks the fallopian tubes. The devices are intended to permanently remain in the patient's body. Some procedures use radio frequency (RF) energy emitted from an implanted device to thermally damage the uterotubal junction and cause it to constrict around a device, e.g., a plug, which is left in place at the junction. Other procedures are available including inserting a tissue fibrosing material into the fallopian tube to encourage fibrous growth to occlude the tube. Ligature procedures to occlude the tubes are also used.

SUMMARY

This invention relates to a medical device and procedure. In general, in one aspect, the invention features a method for female sterilization. With respect to each fallopian tube, a device is transcervically inserted into the fallopian tube and an immediate sterilization procedure is performed with the device. A radio frequency (RF) applicator is positioned at a tubal ostium of the fallopian tube, and current is passed through the RF applicator to destroy tissue to a known depth and to precipitate a healing response in surrounding tissue that over time scars. The scar tissue permanently occludes the fallopian tube. The immediate sterilization procedure provides immediate and at least temporary sterilization and the scar tissue resulting from the application of current through the RF applicator provides permanent tubal occlusion.

Implementations of the invention can include one or more of the following features. Performing an immediate sterilization procedure can include inserting an occlusion device into the fallopian tube, where the occlusion device immediately occludes the fallopian tube. The occlusion device can be formed from a biodegradable material and is configured to provide tubal occlusion for at least as long as a period of time required for the scar tissue to permanently occlude the fallopian tube.

The occlusion device can be formed from a non-biodegradable material. The occlusion device can be configured as a screw and can be rotated within the tube upon insertion such that threads included on an exterior service of the device are threaded into surrounding tissue, providing a tight seal between the device and the tissue. In another implementation, the device can be configured as a plug including one or more fixation elements configured to fixate onto surrounding tissue.

The RF applicator can include an RF applicator head including an electrode carrier with one or more bipolar electrodes thereon and having an open and a closed position. The RF applicator can be positioned such that a distal tip of the RF applicator head in a closed position advances into the tubal ostium. The RF applicator head can be deployed into an open position such that the RF applicator head approximates the shape of the uterine cavity in a region of the tubal ostium. Current is passed through the one or more bipolar electrodes to the tubal ostium to destroy the tissue to a known depth. An illuminator and an optical instrument can be advanced into the uterine cavity. Positioning the RF applicator head at the tubal ostium of a fallopian tube can include using the optical instrument to visualize the tubal ostium.

Performing an immediate sterilization procedure can include inserting an agent into the fallopian tube, where the agent disrupts the cilia and substantially prevents sperm capacitation from occurring for at least a period of time. In one implementation the agent includes isopropyl alcohol.

In general, in another aspect, the invention features a method for fallopian tubal occlusion. A device is transcervically inserted into a fallopian tube where the device occludes the fallopian tube. A radio frequency (RF) applicator is transcervically positioned at a tubal ostium of the fallopian tube. Current is passed through the RF applicator to destroy tissue to a known depth and to precipitate a healing response in surrounding tissue that over time scars. The scar tissue permanently occludes the fallopian tube. The device inserted into the fallopian tube provides immediate and at least temporary tubal occlusion, and the scar tissue resulting from the application of current through the RF applicator provides permanent tubal occlusion.

Implementations of the invention can include one or more of the following features. The device can be inserted into the fallopian tube first and the RF applicator inserted second and positioned proximal the device. Alternatively, the RF applicator can be inserted first and current passed through the RF applicator; the device subsequently can be inserted into the fallopian tube. The device can be inserted distal or proximal to a region ablated by the RF applicator.

The device can be formed at least partially from a biodegradable material and configured to provide tubal occlusion for at least as long as a period of time required for the scar tissue to permanently occlude the fallopian tube. For example, in one implementation the device is configured to provide tubal occlusion for at least three months from the date of insertion. In another implementation, the device is formed from a non-biodegradable material. The device can be configured as a screw and can be rotated within the tube upon insertion, such that threads included on an exterior surface of the device are threaded into surrounding tissue providing a tight seal between the device and the tissue. In another implementation, the device is configured as a plug including one or more fixation elements configured to fixate into surrounding tissue.

The RF applicator can include an RF applicator head including an electrode carrier with one or more bipolar electrodes thereon and having an open and a closed position. The RF applicator can be positioned such that a distal tip of the RF applicator head in a closed position advances into the tubal ostium. The RF applicator head can be deployed into an open position, such that the RF applicator head approximates the shape of the uterine cavity in a region of the tubal ostium. Current can be passed through the one or more bipolar electrodes to the tubal ostium to destroy the tissue to a known depth. Passing current through the one or more bipolar electrodes to the tubal ostium to destroy tissue can include vaporizing endometrium and destroying superficial myometrium.

Suction can be applied through the electrode carrier to draw surrounding tissue into contact with the electrodes and to draw moisture generated during ablation away from the electrodes to substantially prevent the formation of a low impedance liquid layer at the electrodes.

Passing current through the one or more bipolar electrodes can include delivering radio frequency energy to the one or more bipolar electrodes. The flow of current into the tissue can be terminated once ablation has approximately reached a predetermined depth of ablation. Before positioning the RF applicator head at the tubal ostium, the uterine cavity can be insufflated. Before passing current through the one or more bipolar electrodes, insufflation can be ceased and the uterine cavity allowed to collapse onto the RF applicator head. The electrode carrier can include a fabric having conductive metallized regions and one or more non-conductive regions formed thereon to create the one or more bipolar electrodes.

An illuminator and an optical instrument can be advanced into the uterine cavity. Positioning the RF applicator head at the tubal ostium of a fallopian tube can include using the optical instrument to visualize the tubal ostium.

In general, in another aspect, the invention features a method for female sterilization. For each of a first and second fallopian tube, an agent is transcervically injected into the fallopian tube. The agent disrupts cilia included in the fallopian tube and substantially prevents sperm capacitation from occurring within the fallopian tube for a period of time. For each of the first and second fallopian tubes, a radio frequency (RF) applicator is transcervically positioned at a tubal ostium of the fallopian tube and current is passed through the RF applicator to destroy tissue to a known depth and to precipitate a healing response in surrounding tissue that over time scars. The scar tissue permanently occludes the fallopian tube. Inserting the agent into the first and second fallopian tubes provides immediate and at least temporary sterilization until the scar tissue resulting from the application of current through the RF applicator provides permanent sterilization.

In one implementation, agent includes isopropyl alcohol. In another implementation, the agent includes methyl cyanoacrylate.

In general, in another aspect, the invention features a method for fallopian tubal occlusion. A device is transcervically inserted through a uterine cavity and into a fallopian tube where the device occludes the fallopian tube. A substantially rigid, curved elongate member including a substantially cylindrically shaped electrode carrier positioned at a distal end, with one or more bipolar electrodes formed thereon, is transcervically inserted into the uterine cavity. The electrode carrier is positioned at a tubal ostium of the fallopian tube, such that a distal end of the electrode carrier advances into the tubal ostium. Radio frequency energy is passed through the one or more bipolar electrodes to the tubal ostium to destroy tissue to a known depth and to precipitate a healing response in surrounding tissue that over time scars and occludes the fallopian tube. The device inserted into the fallopian tube provides immediate and at least temporary tubal occlusion and the scar tissue resulting from the application of current through the electrodes provides permanent tubal occlusion.

Implementations of the invention can include one or more of the following features. Passing radio frequency energy through the one or more bipolar electrodes can include passing a current at an initial current level through the one or more bipolar electrodes to the target tissue site to apply an initial power density to destroy tissue for an initial time period. After the initial time period, the power density can be ramped up by increasing the current passed through the one or more bipolar electrodes to the target tissue site for a second time period. Ramping up the power density can include gradually increasing the current over the second time period. In another implementation, ramping up the power density can include suddenly increasing the current from the initial current level to a second current level and applying the second current level for the second time period.

An impedance level can be monitored at an interface between the electrode carrier and the tubal ostium. The initial time period can be a time period after which a threshold decrease in the impedance level from an initial impedance level is detected. The initial time period can be determined empirically as a time period after which an initial depth of tissue destruction has been achieved.

In general, in another aspect, the invention features a system for fallopian tubal occlusion. The system includes a tubal occlusion device configured to be transcervically positioned within a fallopian tube. The device is configured to completely occlude the fallopian tube and includes one or more fixation elements configured to fixate the device to surrounding tissue. The system further includes an ablation device configured to provide radio frequency energy to tissue at a tubal ostium of the fallopian tube to precipitate a healing response in surrounding tissue that over time scars and scar tissue occludes the fallopian tube. The device includes a distal end and a proximal end. The distal end includes an electrode carrier with one or more bipolar electrodes thereon and in an open condition is shaped to approximate a uterine cavity in a region of a tubal ostium of a fallopian tube to be occluded. The tubal occlusion device provides immediate tubal occlusion at least until the scar tissue resulting from the ablation device permanently occludes the fallopian tube.

Implementations of the invention can include one or more of the following features. The tubal occlusion device can be at least partially biodegradable. In one implementation, the tubal occlusion device includes a body configured to occlude the fallopian tube and one or more fixation elements configured to fixate the body to surrounding tissue. The one or more fixation elements can include threads formed on an exterior surface of at least a portion of the body. The threads can be configured to thread into the surrounding tissue upon rotation of the tubal occlusion device, thereby affixing the body to the surrounding tissue and forming a seal between the body and the surrounding tissue sufficient to prevent sperm from traveling past the tubal occlusion device. The one or more fixation elements comprise barbs formed on an exterior surface of at least a portion of the body. The barbs can be configured to pierce into the surrounding tissue, thereby affixing the body to the surrounding tissue and forming a seal between the body and the surrounding tissue sufficient to prevent sperm from traveling past the tubal occlusion device.

The system can further include a source of radio frequency energy electrically coupled to the one or more bipolar electrodes included in the ablation device. A controller configured to control the delivery of radio frequency energy to the one or more bipolar electrodes can be included, such that passing radio frequency energy through the one or more bipolar electrodes to the tubal ostium can be controlled to destroy tissue to a known depth that precipitates a healing response in surrounding tissue.

The system can include a vacuum source operable to draw the tissue into contact with the one or more bipolar electrodes, to draw moisture generated during delivery of the radio frequency energy to the one or more bipolar electrodes away from the one or more bipolar electrodes, and to substantially eliminate liquid surrounding the one or more bipolar electrodes.

Passing radio frequency energy through the one or more bipolar electrodes to the tubal ostium destroying tissue can include vaporizing the endometrium and destroying superficial myometrium. The electrode carrier can include a structural support member within a fabric sheath having conductive metallized regions and having one or more non-conductive regions formed thereon to create the one or more bipolar electrodes. The structural support member can include flexible members movable between a closed condition and the open condition.

The system can further include an illumination source electrically coupled to the distal end of the ablation device to illuminate the uterus. An optical instrument can be electrically coupled to the distal end of the ablation device to provide images of the uterus.

In general, in another aspect, the invention features a system for fallopian tubal occlusion including a tubal occlusion device and an ablation device. The tubal occlusion device is configured to be transcervically positioned within a fallopian tube and completely occludes the fallopian tube. The tubal occlusion device includes one or more fixation elements configured to fixate the device to surrounding tissue. An ablation device is configured to provide radio frequency energy to tissue at a tubal ostium of the fallopian tube to precipitate a healing response in surrounding tissue that over time scars and scar tissue occludes the fallopian tube. The ablation device includes an elongate member having a distal end, a proximal end and a central interior including at least a first lumen operable to couple to a vacuum source and to draw moisture way from one or more electrodes included in an electrode carrier positioned at the distal end of the elongate member and at least a second lumen configured to receive a hysteroscope. The first lumen and the second lumen can be the same lumen or can be separate lumens. The ablation device further includes an electrode carrier attached to the distal end of the elongate member, and includes one or more bipolar electrodes formed thereon and operable to couple to a radio frequency energy generator. One or more conductors are included, extending from the electrode carrier to the proximal end of the elongate member and configured to connect to a controller operable to control the delivery of radio frequency energy to the one or more bipolar electrodes. The elongate member is a substantially rigid member configured with a curve to facilitate advancement of the distal end transcervically through a uterus and into a region of a tubal ostium of a fallopian tube to be occluded. The tubal occlusion device provides immediate tubal occlusion at least until the scar tissue resulting from the ablation device permanently occludes the fallopian tube.

Implementations of the invention can include one or more of the following features. A hysteroscope can be positioned within the first lumen of the elongate member, such that a distal end of the hysteroscope is positioned approximately just proximal of a distal end of the electrode carrier. The hysteroscope can be substantially rigid and configured with a similar curve to the curve of the elongate member. In another implementation, the hysteroscope can be substantially flexible and can flex to accommodate the curve of the elongate member.

The electrode carrier can include an approximately cylindrically shaped support member within a fabric sheath having conductive metallized regions and one or more non-conductive regions formed thereon to create the one or more bipolar electrodes. The support member can be formed from a plastic material, the fabric sheath can be formed from a polymer mesh and the conductive metallized regions can be formed by selectively coating the polymer mesh with gold. The electrode carrier can be an approximately cylindrically shaped member including a metallic mesh insert molded in a support member formed from a plastic material/The metallic mesh can form conductive regions and the plastic material can form non-conductive regions thereby creating the one or more bipolar electrodes.

The system can further include a vacuum source in fluid communication with the first lumen included in the elongate member and operable to draw tissue surrounding the electrode carrier into contact with the one or more bipolar electrodes. The vacuum source can further draw moisture generated during delivery of the radio frequency energy to the one or more bipolar electrodes away from the one or more bipolar electrodes and substantially eliminate liquid surrounding the one or more bipolar electrodes. The system can further include a radio frequency energy generator coupled to the one or more bipolar electrodes through the one or more conductors, where the radio frequency energy generator includes or is coupled to a controller operable to control the delivery of radio frequency energy to the one or more bipolar electrodes.

Implementations of the invention can realize one or more of the following advantages. After the relatively quick, doctor's office procedure, the patient can leave feeling assured that the sterilization has been immediately achieved. There is no need for the patient to continue to use birth control for a period of time until the effects of the procedure are achieved; the effects are immediate. The tubal occlusion procedure described is minimally invasive: the tubal occlusion tool can be introduced into the patient's uterine cavity transcervically and requires no abdominal incision. In some implementations, the procedure does not leave any foreign objects in the patient's body, minimizing the risk of infection. The procedure can be performed quickly, the actual duration of ablation being approximately one minute per fallopian tube.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 10B is a cutaway view of a portion of the tubal occlusion device shown in FIG. 8A.

FIG. 10C is a cross-sectional view of an RF applicator head of the tubal occlusion device shown in FIG. 8A.

Like reference symbols in the various drawings indicate like elements.

DETAILED DESCRIPTION

Apparatus and procedures for occlusion of a female's fallopian tubes are described that provide a minimally invasive alternative for female sterilization. The procedure includes two parts; one part is directed at providing immediate sterilization, by either immediate tubal occlusion or otherwise, and the other part is directed at providing permanent tubal occlusion for permanent sterilization.

Conventional tubal occlusion procedures typically require the female patient to wait several weeks before she can be assured that tubal occlusion has been achieved. For example, a period of time generally must expire before scar tissue or fibrous ingrowth has progressed to completely occlude the fallopian tubes. During that period of time, the female is not sterile and must use an alternate form of birth control. In some situations, where the sterilization procedure is being performed to prevent a pregnancy that could endanger the health of the female, having a period of time before sterility is achieved can be risky.

The procedure described herein provides the female patient with immediate sterility that will endure at least as long as the period of time required for permanent tubal occlusion to occur. In one implementation, immediate sterility is provided by inserting a device into each fallopian tube to provide immediate occlusion. In another implementation, immediate sterility is provided by injecting an agent into the fallopian tubes that disrupts the cilia and prevents sperm capacitation.

It should be noted that although the immediate sterilization procedure generally provides only temporary sterility, and may therefore be considered by some as a contraceptive procedure, as used throughout this specification, the immediate sterilization procedure is a procedure that provides immediate sterilization (i.e., immediately renders the female unable to get pregnant) and that endures at least until the permanent sterilization procedure has taken effect. The immediate sterilization generally provides only temporary sterility, although can in some cases also provide permanent sterility, whether advertently or inadvertently.

In one implementation, permanent sterility can be permanent tubal occlusion provided by applying radio frequency (RF) energy to the corresponding fallopian tubes, e.g., the tubal ostia. The RF energy destroys the surrounding tissue to a known depth and precipitates a healing response in the surrounding tissue. The tissue scars over time and the scar tissue permanently occludes the fallopian tube. The immediate sterilization used in conjunction with an RF ablation type permanent occlusion procedure, as just described, provides immediate sterilization that lasts at least until the scar tissue has permanently occluded the fallopian tubes.

Figure 1A:
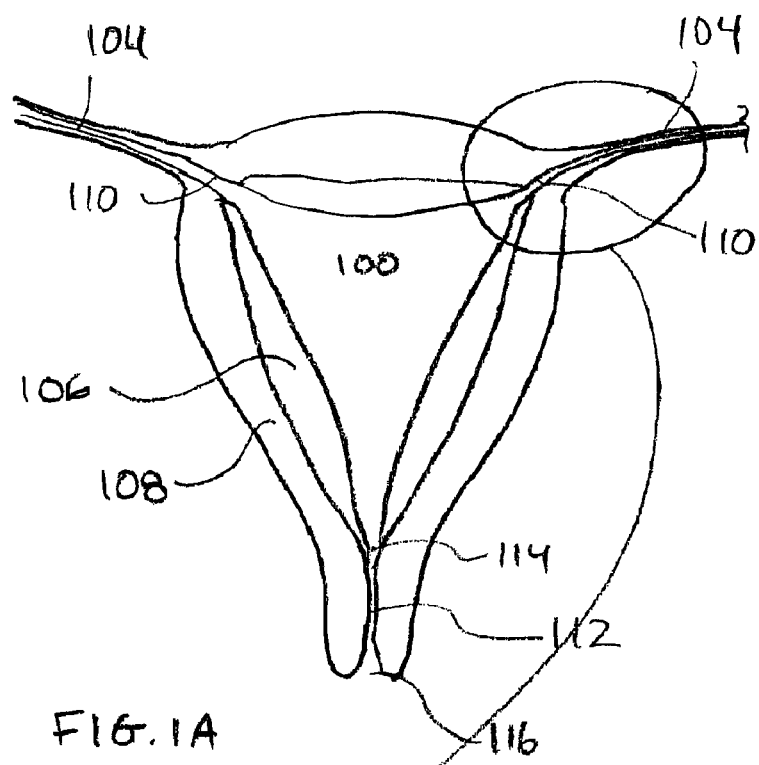
FIG. 1A is a schematic representation of a uterus.

Referring to FIG. 1A, a schematic representation of a uterine cavity 100 and portions of fallopian tubes 104 is shown. The uterine cavity 100 is surrounded by uterine tissue, namely endometrial tissue 106 and myometrial tissue 108. The fallopian tubes 104 connect to the uterine cavity 100 at the tubal ostia 110. Occluding the tubal ostia 110 prevents sperm from entering the fallopian tubes 104 and fertilizing an egg, thereby sterilizing the female. The uterine cavity 100 connects to the cervix 112 at the internal os 114, and the cervix 112 connects to the vagina at the external os 116.

Figure 1B:
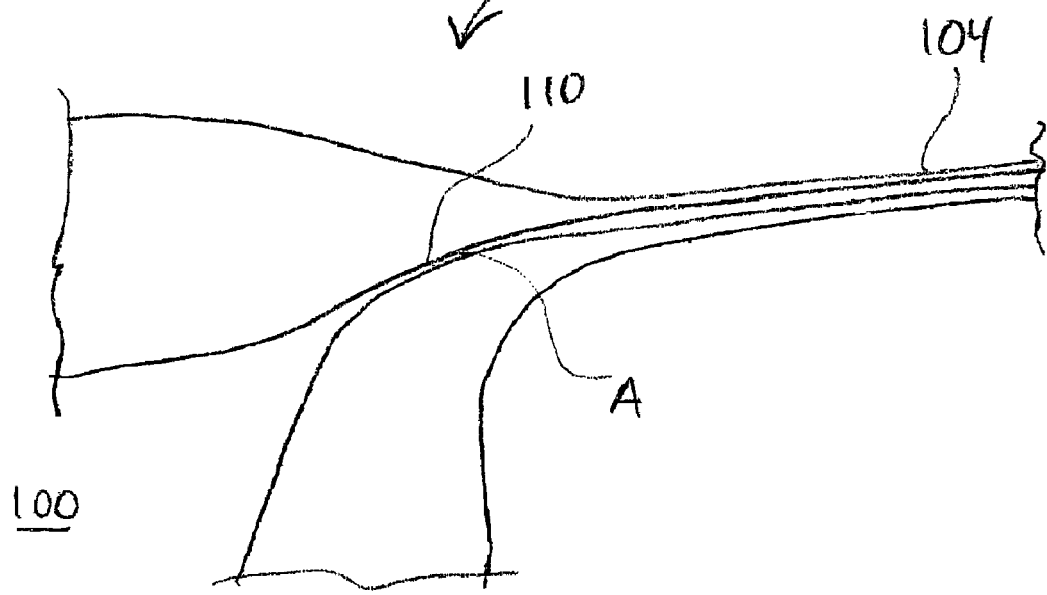
FIG. 1B is an enlarged view of a portion of the schematic representation of a uterus shown in FIG. 1A.

FIG. 1B shows an enlarged view of one region of the uterine cavity 100, right tubal ostium 110 and right fallopian tube 104. Locator A is included on the figure as a possible position for performing temporary or permanent sterilization procedures, as shall be discussed in further detail below.

Figure 2:
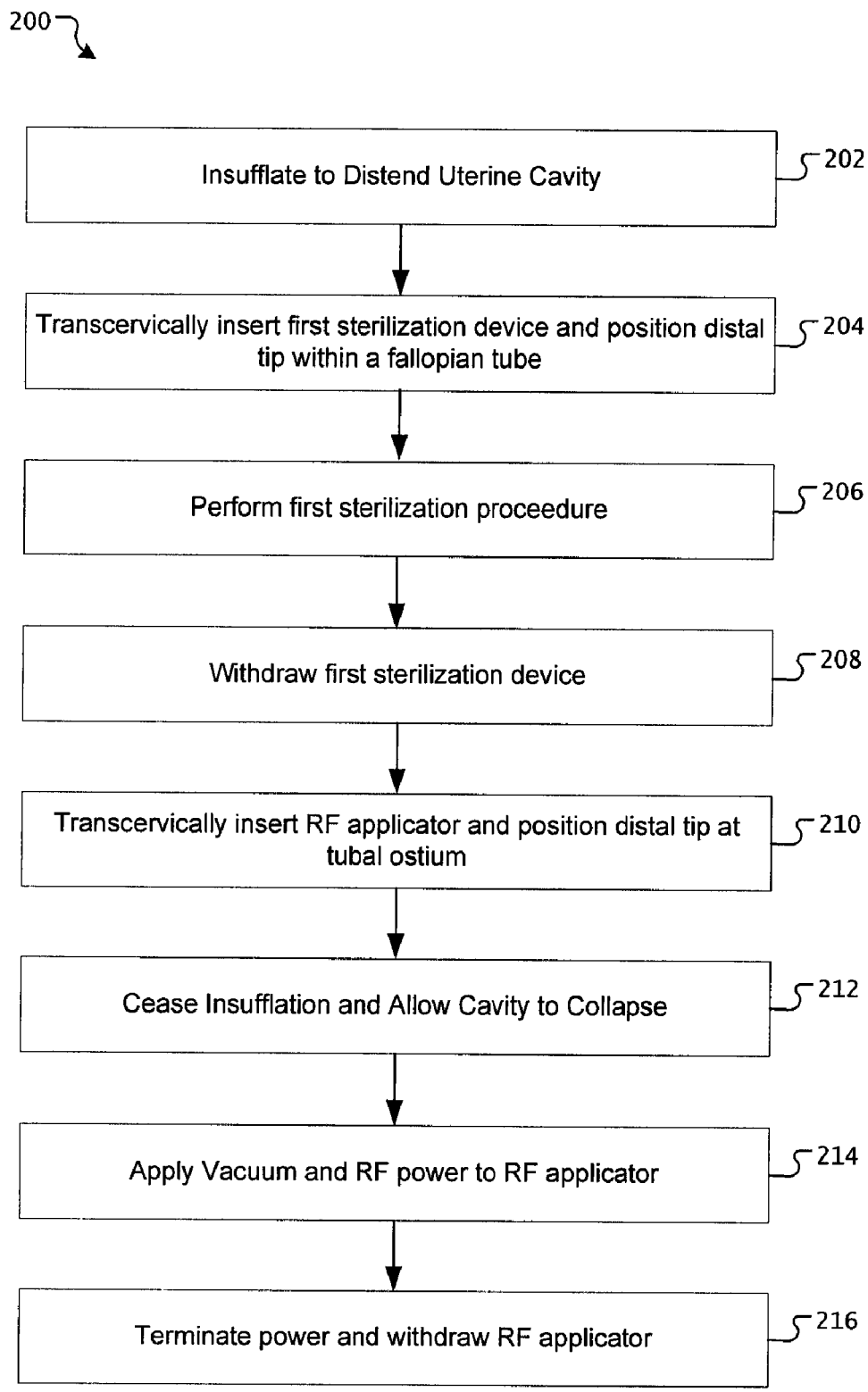
FIG. 2 is a flowchart showing a process for one implementation of a two-part sterilization procedure.

Referring to FIG. 2, one implementation of a procedure 200 for performing a two part sterilization procedure, including one part for immediate sterilization and another part for permanent sterilization, is shown. In the example procedure 200 shown in this flowchart, the immediate sterilization part of the procedure is performed first and the permanent sterilization part is performed second. However, in another implementation, the two parts of the procedure can be performed in the reverse order and still achieve the desired results.

A gas, e.g., carbon dioxide, is delivered into the uterine cavity 100 to insufflate and distend the uterine cavity 100 (step 202). In one implementation, a device fluidly coupled to a gas source can be transcervically positioned such that a distal end of the device is at the internal os 114 and the gas then delivered into the uterine cavity 100.

An immediate sterilization device is then transcervically inserted into the uterine cavity and a distal tip of the device is positioned within a fallopian tube (step 204). In one implementation, the device is positioned at approximately locator A, as shown in FIG. 1B. Although in other implementations, the device can be positioned proximal or distal to locator A. Optionally, the operator of the device can visualize the target tubal ostium 110 on a monitor using images provided by a camera included within either the immediate sterilization device or an endoscope. The endoscope can be inserted along with the immediate sterilization device and in one implementation includes a working channel, such that the immediate sterilization device can be advanced through the working channel of the endoscope.

The immediate sterilization part of the procedure is performed once the distal tip of the immediate sterilization device is positioned within the fallopian tube 104 (step 206). In one implementation, the immediate sterilization part of the procedure includes depositing a tubal occlusion device within the fallopian tube 104 to provide immediate and at least temporary occlusion. In another implementation, the immediate sterilization part of the procedure includes injecting an agent into the fallopian tube 104 that disrupts the cilia and thereby immediately and at least temporarily prevents sperm capacitation. The immediate sterilization part of the procedure are discussed in further detail below.

The immediate sterilization device is withdrawn from the uterine cavity once the immediate sterilization part of the procedure is complete (step 208). An RF applicator is transcervically inserted and a distal tip of the RF applicator is positioned at the ablation region (step 210). In one implementation, the ablation region is the tubal ostium at proximal to locator A as shown in FIG. 1B, although in other implementations, the ablation region can be positioned proximal or distal to locator A. If an endoscope including a working channel is used, the immediate sterilization device can be withdrawn from the working channel and replaced by the RF applicator.

Insufflation is ceased and the uterine cavity 100 is allowed to collapse onto the RF applicator (step 212). Vacuum can be applied to the RF applicator via a suction/insufflation tube to draw the surrounding tissue into contact with electrodes included in the RF applicator (step 214). An RF generator is turned on to provide RF energy to the electrodes (step 214). The RF energy is ceased once the desired amount of tissue has been ablated (step 216). In one implementation, 5.5 watts of RF power is supplied per square centimeter of electrode surface area until a predetermined impedance threshold is reached, at which point power is terminated.

The procedure is repeated for the second fallopian tube. In one implementation, immediate sterilization procedures are performed on each of the two fallopian tubes, followed by the RF ablation procedure being performed on each of the two fallopian tubes. For example, the uterine cavity 100 can be insufflated a second time and the RF applicator rotated approximately 180° and positioned at the other tubal ostium. The above described ablation procedure is then repeated to ablate tissue at the other tubal ostium 110. The RF applicator is then withdrawn from the female's body.

Immediately following the two-part procedure, the female is sterile. After several weeks, the healing and scarring responses of the tissue at the tubal ostia 110 permanently occlude the fallopian tubes 104 without any incisions into the female's abdomen. Prior to that occurring, the immediate sterilization procedure provides immediate and at least temporary sterilization. The procedure is fast, minimally invasive and effective.

In one implementation, first the tubal occlusion device is inserted into and deposited within the fallopian tube. Second, an RF applicator is then positioned proximal to the tubal occlusion device at the tubal ostium of the fallopian tube, and current is passed through the RF applicator to destroy the surrounding tissue and precipitate scar tissue growth. The tubal occlusion device can be formed from a biodegradable material, such that over time after the fallopian tubes are permanently occluded by the scar tissue, the tubal occlusion device biodegrades and is naturally eliminated from the female. Alternatively, the tubal occlusion device can be formed from a non-biodegradable material and remain permanently in the fallopian tube.

In another implementation, the RF ablation can occur within a region of the fallopian tube that is beyond the tubal ostia. The RF ablation can occur first and then a tubal occlusion device can be inserted into the fallopian tube proximal to the ablation region and configured to occlude the tube. If the tubal occlusion device is formed from a non-biodegradable material, the tubal occlusion device can then be manually removed after the scar tissue has permanently occluded the fallopian tube, naturally work loose and be expelled from the body or remain permanently.

In another implementation, the tubal occlusion device is formed from a combination of biodegradable and non-biodegradable material. The device includes a body and one or more fixating elements. The body can be formed from a non-biodegradable material and the fixating elements formed from a biodegradable material. Over time, as the biodegradable material degrades, the fixating elements no longer affix the body to surrounding tissue, and the remainder of the device, i.e., the non-biodegradable body, can work loose and be naturally expelled from the female.

In one implementation, the immediate sterilization device and the RF applicator are combined into a single device that can perform both the immediate and permanent sterilization procedures. For example, in one implementation, a device to affect immediate sterilization can be loaded on the distal tip of a catheter. The RF applicator can be located proximal to the device that affects immediate sterilization.

Immediate Occlusion Devices

Figure 3A:
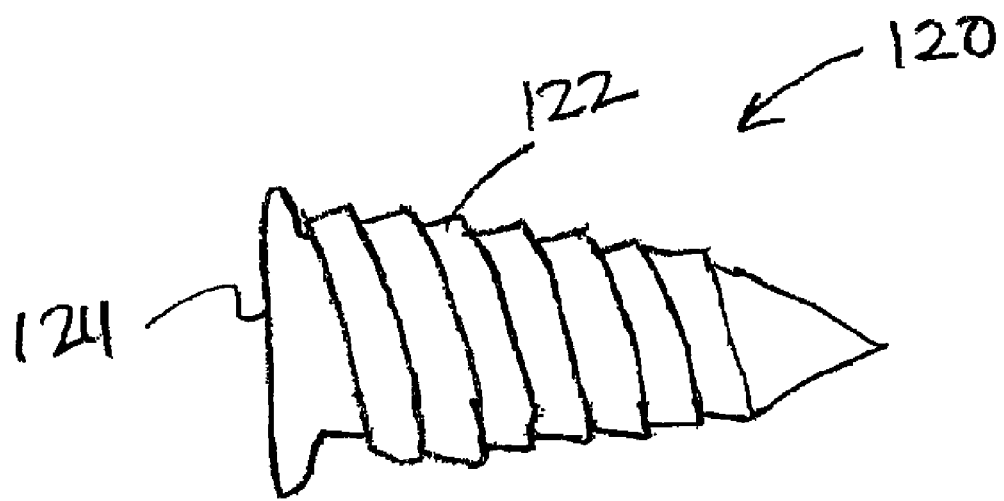
FIGS. 3A and 3B show embodiments of an immediate sterilization device.
Figure 3B:
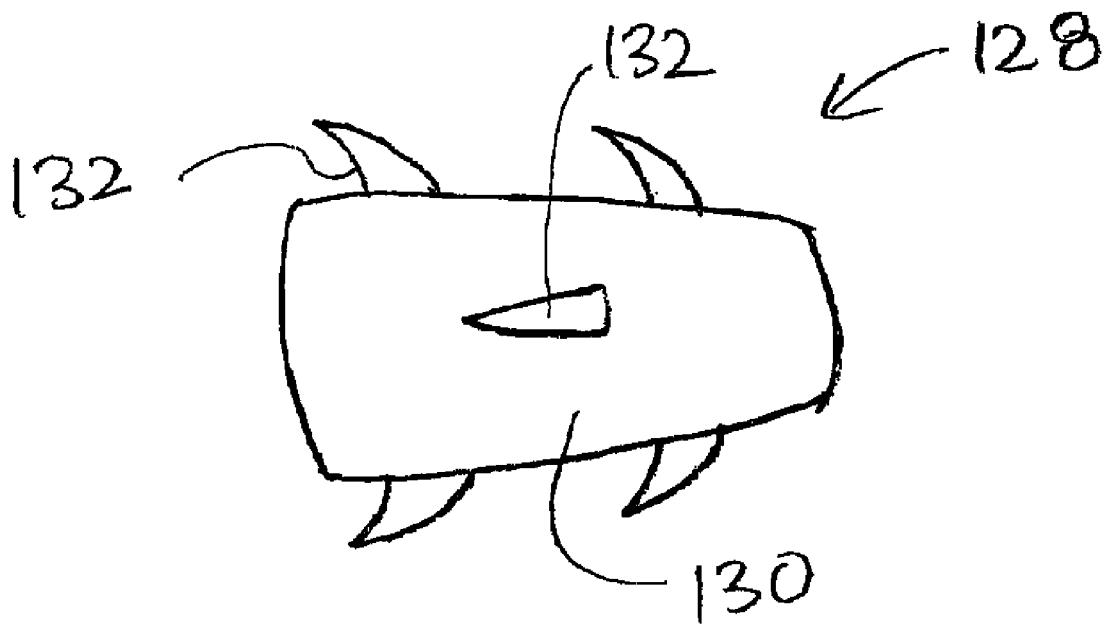

Referring to FIGS. 3A-B, example embodiments of a device that can be inserted into a fallopian tube to provide immediate and at least temporary tubal occlusion are shown. Referring particularly to FIG. 3A, the tubal occlusion device 120 includes a tapered, threaded body 122 and a head 124. The head 124 can be configured to mate with an insertion tool, such that the tubal occlusion device 120 can be rotated by the insertion tool within the fallopian tube to in effect screw the device into the surrounding tissue. That is, the fixating elements are the threads on the threaded body 122 and can screw into the surrounding tissue as the tubal occlusion device 120 is rotated, thereby providing a secure fit. The tubal occlusion device 120 is configured such that the dimensions allow the tubal occlusion device 120 to be securely screwed into the fallopian tube with a tight fit that does not permit the passage of fluid including sperm past the tubal occlusion device 120. The fallopian tube is thereby effectively occluded. In one implementation, on outer diameter of the tubal occlusion device 120 is in the range of 0.1 to 2.5 mm, and preferably 0.5 to 1.5 mm.

In one implementation, the tubal occlusion device 120 is made from a biodegradable material. The material maintains its integrity for at least the first several weeks and does not begin to biodegrade to the point where tubal occlusion is compromised until the period of time required for permanent tubal occlusion by way of the ablation part of the procedure has taken effect. An example of a biodegradable material is polyglycolic acid (PGA), a synthetic absorbable polymer, although other materials can be used.

In another implementation, the tubal occlusion device 120 is non-biodegradable. Securing the tubal occlusion device 120 into the fallopian tube by way of the threaded connection will at least ensure that the tubal occlusion device 120 will remain in place for several months. Accordingly, even if the tubal occlusion device 120 does eventually work loose from the fallopian tube, by then permanent occlusion will have occurred by way of the ablation part of the procedure. An example of a material from which the tubal occlusion device 120 can be made is polyethylene terephthalate (PET), although other materials can be used.

Referring now to FIG. 3B, another example of an embodiment of an immediate tubal occlusion tubal occlusion device 128 is shown. The tubal occlusion device 128 includes a body 130 and multiple fixating elements, in this embodiment, barbs 132 positioned thereon. The barbs 132 are configured to pierce into and grasp surrounding tissue when the tubal occlusion device 128 is inserted into the fallopian tube 110. The body 130 can be tapered toward a distal end. When inserted, the barbs 132 securely hold the tubal occlusion device 128 within the fallopian tube. The body 130 is configured with dimensions such that a tight fit is formed with the surround tissue and fluid including sperm cannot pass beyond the tubal occlusion device 128. The fallopian tube 110 is thereby effectively occluded. In one implementation, on outer diameter of the body 130 is in the range of 0.1 to 2.5 mm, and preferably 0.5 to 1.5 mm.

In one implementation, the tubal occlusion device 128 is formed from a biodegradable material. The material maintains its integrity for at least the first several weeks and does not begin to biodegrade to the point where tubal occlusion is compromised until at the period of time required for permanent tubal occlusion by way of the ablation part of the procedure has taken effect. An example of biodegradable material is PGA, although other materials can be used.

In another implementation, the tubal occlusion device 128 is non-biodegradable. Securing the tubal occlusion device 128 into the fallopian tube by way of the barbs 132 at least ensures that the tubal occlusion device 128 will remain in place for several months. Accordingly, even if the tubal occlusion device 128 does eventually work loose from the fallopian tube, by that time permanent occlusion will have occurred by way of the ablation part of the procedure. An examples of material from which the tubal occlusion device 128 can be made is PET, although other materials can be used.

In another implementation, just the fixating element, i.e., the barbs 132, are formed from a biodegradable material. Once the barbs 132 have biodegraded to the point where the connection to the fallopian tube terminates, the non-biodegradable body 130 eventually dislodges from the fallopian tube 110 and is naturally eliminated from the female's body.

Figure 4A:
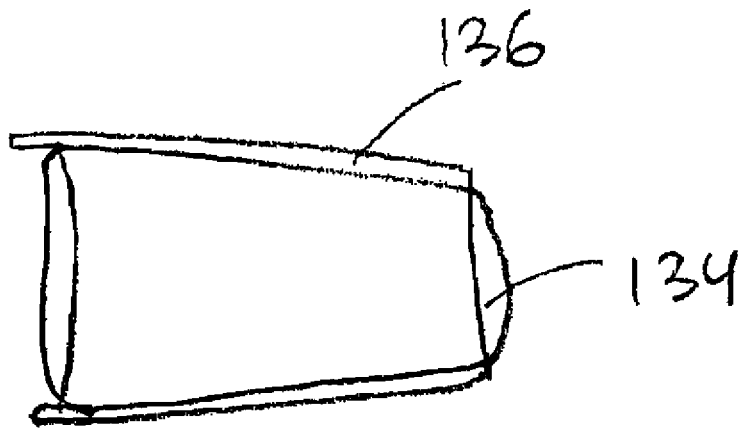
FIGS. 4A-C show an alternative embodiment of an immediate sterilization device.
Figure 4B:
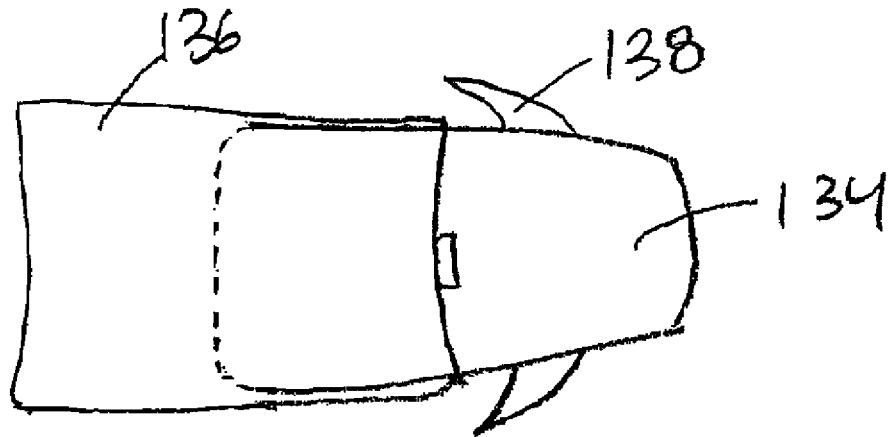
Figure 4C:
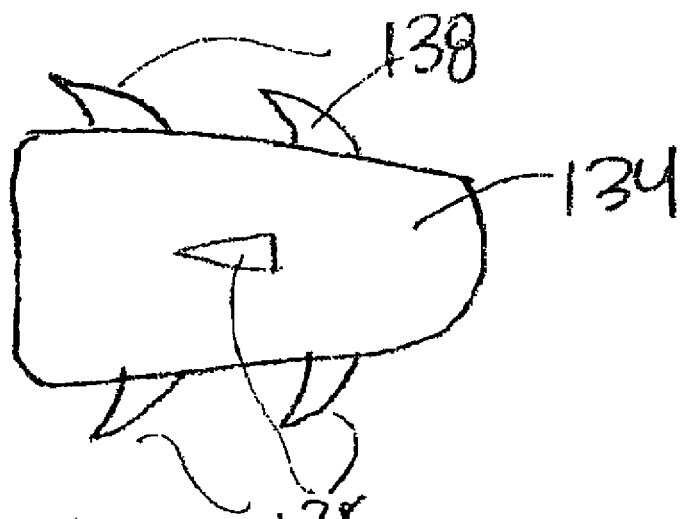

Referring now to FIGS. 4A-C, another example of an immediate occlusion device is shown. In this example, the tubal occlusion device 134 is initially inserted into the fallopian tube within a sheath 136. Once the tubal occlusion device 134 has been positioned at the desired location, the sheath 136 is withdrawn, exposing one or more fixating elements. In this example, the fixating elements are barbs 138. The barbs 138 can be formed from a compressible material that springs into shape once the sheath 136 is removed. In one example, the barbs 138 are formed from a shape memory material, such as Nitinol, an acronym for NIckel TItanium Naval Ordnance Laboratory. Nitinol is a family of intermetallic materials that contains nearly equal mixture of nickel (55 wt. %) and titanium; other elements can be added to adjust or "tune" the material properties. An insertion tool configured to position the tubal occlusion device 134 enclosed within the sheath 136 can include a mechanism for retracting and then withdrawing the sheath 136.

In one implementation, the "device" implanted to provide temporary occlusion can instead be an adhesive that at least temporarily adheres to the tissue within the fallopian tube 104 thereby occluding the tube. An example adhesive is methyl cyanoacrylate (MCA), although another adhesive can be used.

Alternate Immediate Sterilization Procedure

Referring again to FIG. 2, in one implementation the immediate sterilization procedure performed at step 206 includes injecting an agent into the fallopian tubes that disrupts the cilia and prevents sperm capacitation. Before entering the ampulla of the fallopian tube, where mammalian fertilization occurs, uncapacitated sperm bind actively to the membranes of the fallopian tube cells in the isthmus preceding the ampulla. The binding is temporary and appears to be broken when the sperm become capacitated. If an agent is injected into the fallopian tube that disrupts the cilia and therefore the capacitation process, the sperm cannot capacitate. Uncapacitated sperm cannot fertilize an egg, and therefore pregnancy is prevented.

In one implementation, the agent includes isopropyl alcohol (IPA). Sufficient IPA is introduced into the intramural/isthmic portion of the fallopian tube to disrupt the cilia such that the cilia cannot reconstruct and function normally for at least as long as required for permanent occlusion to take effect from the ablation part of the procedure. For example, in one implementation, approximately 1.0-3.0 milliliters of agent can be injected per fallopian tube. In other implementations, another agent, such as a sclerosing agent, can be used. Another example of an agent is methyl cyanoacrylate (MCA).

Permanent Tubal Occlusion Devices

As described above, the permanent sterilization part of the procedure can involve applying a RF applicator to the fallopian tube and ablating the surrounding tissue to promote scar tissue growth. The RF applicator can be included in an ablation device. Example embodiments of tubal occlusion devices that can include the RF applicator are described below. However, other configurations of ablation devices can be used, and the ones described herein are illustrative examples.

Example Device #1

Figure 5A:
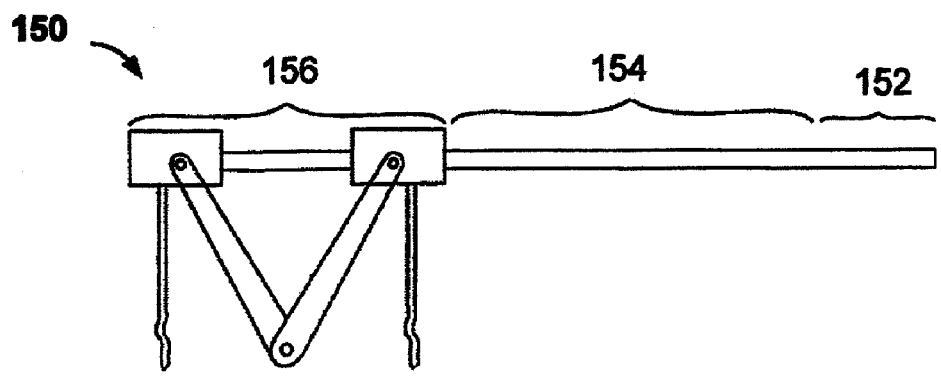
FIG. 5A shows a side view of a tubal occlusion device.
Figure 5B:
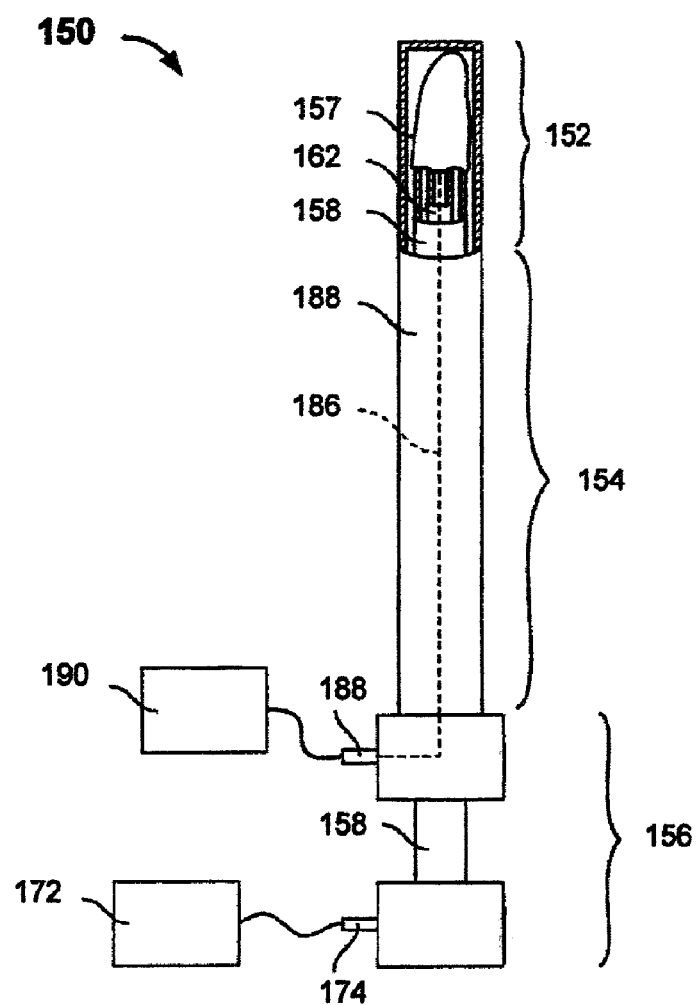
FIG. 5B shows a top view of the tubal occlusion device of FIG. 5A with an RF applicator head in a closed position.
Figure 5C:
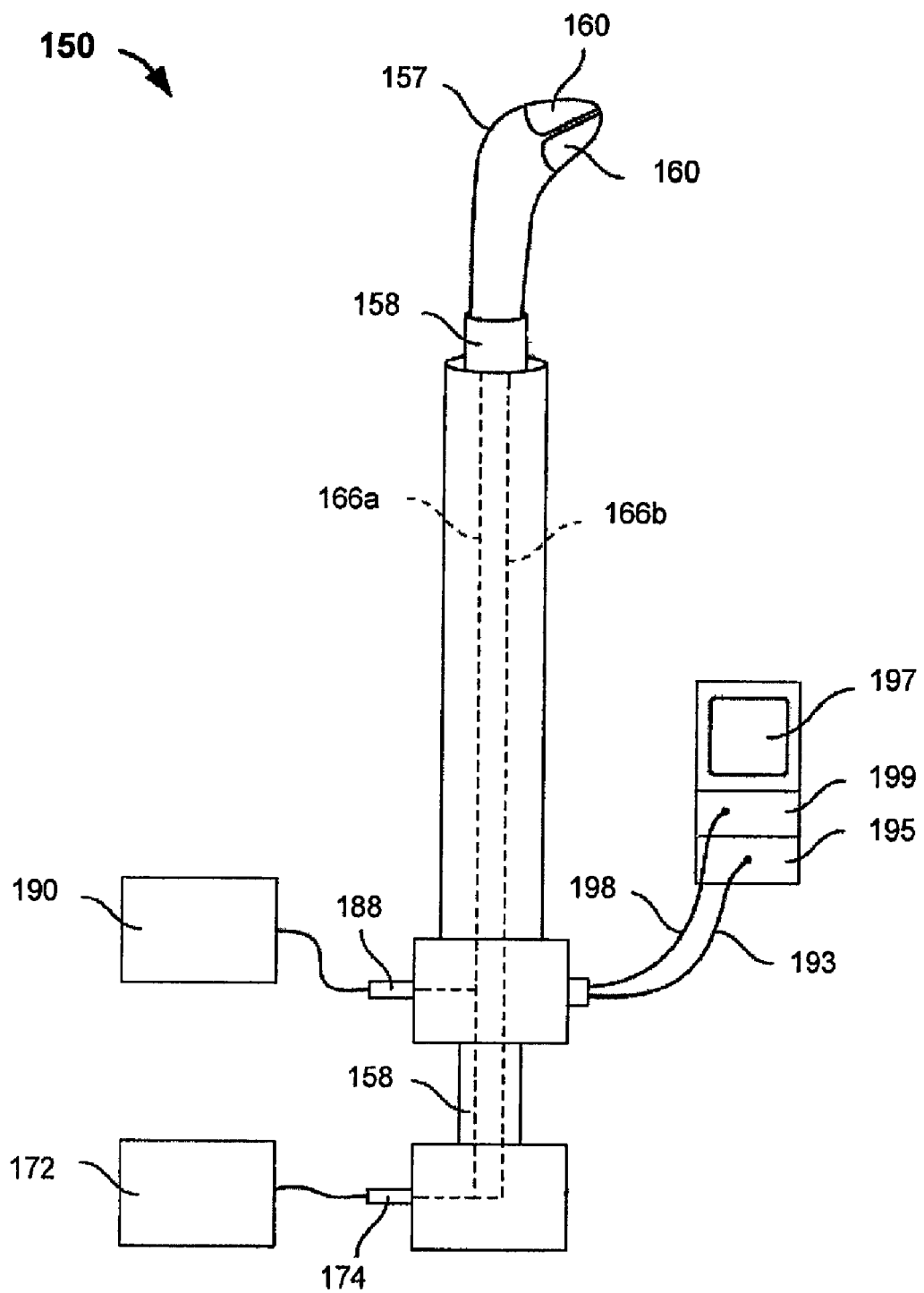
FIG. 5C shows a top view of the tubal occlusion device of FIG. 5A with the RF applicator head in an open position.

Referring to FIGS. 5A-C, one embodiment of an ablation device 150 is shown, which is described further in U.S. patent application Ser. No. 11/019,580, entitled "Method and System for Transcervical Tubal Occlusion", filed by Sampson et al, on Dec. 20, 2004, the entire contents of which are hereby incorporated by reference herein. The ablation device 150 includes generally three major components: the RF applicator head 152, a main body 154, and a handle 156. FIG. 5A shows a side view of the ablation device 150 and FIGS. 5B and 5C show top views. FIG. 5B shows the ablation device 150 with the RF applicator head 152 in a closed position within a sheath 154 and FIG. 5C shows the RF applicator head 152 in an open position outside of the sheath 154. The RF applicator head 152 includes an electrode carrier 157 mounted to the distal end of a shaft 158 and electrodes 160 formed on the surface of the electrode carrier 157. An RF generator 172 can be electrically connected to the electrodes 160 to provide mono-polar or bipolar RF energy to them.

Figure 6A:
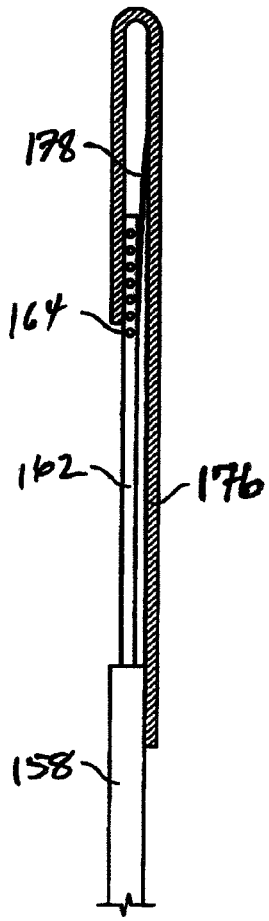
FIGS. 6A and 6B show one embodiment of a structural body of an RF applicator head in closed and open positions respectively.
Figure 6B:
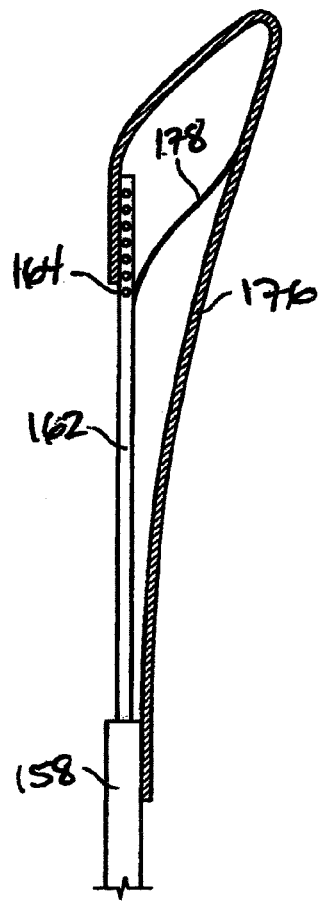

The main body 154 includes the shaft 158, an elongate member having a hollow interior. In one embodiment, the shaft 158 is approximately 30 centimeters long and has a cross-sectional diameter of approximately 4 millimeters. Referring to FIGS. 5B, 6A and 6B, extending through the shaft 158 is a suction/insufflation tube 162 having a plurality of holes 164a formed in its distal end.

Referring particularly to FIG. 5C, electrode leads 166a and 166b extend through the shaft 158 from the distal end to the proximal end of the shaft 158. At the distal end of the shaft 158, each of the leads 166a, 166b is coupled to a respective one of the electrodes 160. At the proximal end of the shaft 158, the leads 166a, 166b are electrically connected to the RF generator 172 by an electrical connector 174. During use, the leads 166a, 166b carry RF energy from the RF generator 172 to the electrodes 160. Each of the leads 166a, 166b is insulated, and the leads 166a and 166b can be connected to opposite terminals of the RF generator 172. When opposite polarity is applied to alternating electrodes or groups of electrodes, an electrode pair (i.e., one positively charged and one negatively charged electrode or group of electrodes) can be referred to as a bipolar electrode. Any references herein to a bipolar electrode refer to such an electrode pair.

Figure 6C:
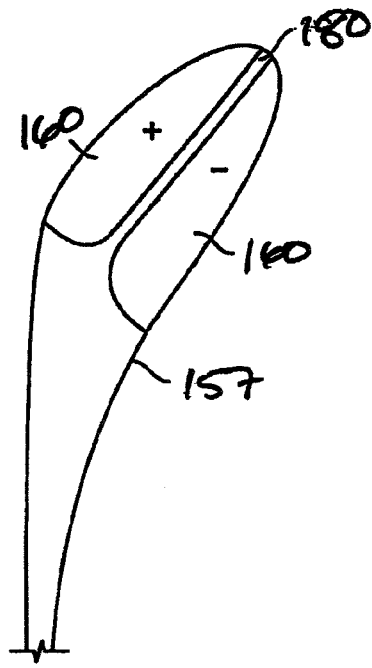
FIG. 6C is a schematic representation of an RF applicator head in an open position.
Figure 6D:
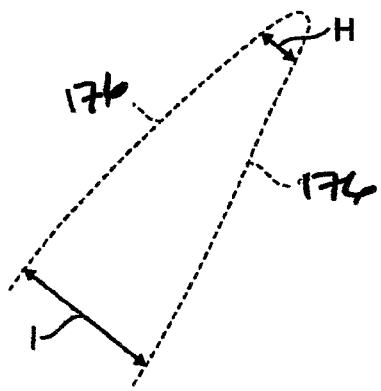
FIG. 6D is a schematic representation of center lines of electrodes of the RF applicator head of FIG. 6C.

Referring to FIGS. 6A-C, the RF applicator head 152 can be shaped to approximate the shape of the region to be ablated. The embodiment of the RF applicator head 152 shown in FIG. 6C has a V-shape, which can fit within a corner of the uterine cavity 100 and reach into the tubal ostium 110. FIGS. 6A and 6B show the RF applicator head 152 without the electrode carrier 157, thereby revealing the structural body of the RF applicator head 152. A flexible member 176 is attached to the distal end of the shaft 158 of the main body and to the distal end of the tube 162. A flexure 178 is attached to the tube 162 and to an inner surface of the flexible member 176. In the closed position shown in FIG. 6A, the flexure 178 is compressed within the space formed between the inner surface of the flexible member 176 and the tube 162, and the shape of the structural body of the RF applicator head 152 is substantially cylindrical. In one embodiment, the flexure 178 and flexible member 176 are made from stainless steel, are approximately 0.012 inches thick and are substantially planar.

The RF applicator head 152 can be deployed into the open position shown in FIG. 6B by moving the tube 162 relative to the shaft 158. In one embodiment, the shaft 158 is pulled toward the proximal end of the shaft, i.e., away from the RF applicator head 152. Movement of the shaft 158, which is connected to the flexible member 176, causes the flexible member 176 to also move in the same direction, causing the flexure 178 to move laterally away from the tube 162. As shown in FIG. 6B, flexible member 176 is deformed outwardly, away from the tube 162, creating the V-shape at the distal end of the RF applicator head 152. The shape of the distal end differs depending on how much the shaft 158 and tube 162 are moved relative to one another.

In an alternative embodiment, the tube 162 can be pushed toward the proximal end of the flexible member 176, i.e., toward the RF applicator head 152, thereby moving the tube 162 relative to the shaft 158. The relative movement has the same effect as described above, that is, the flexible member 176 is deformed outwardly, creating a V-shape at the distal end.

FIG. 6C shows the distal end of the RF applicator head 152 with the electrode carrier 157 over the structural body. The electrode carrier 157 can be formed of a fabric that is stretched over the structural body; the fabric is metallized in the regions forming the electrodes 160. The electrodes 160 are conductive and can alternate between positive and negative polarity (an electrode pair being a "bipolar electrode" as described above). In the embodiment depicted, there are four electrodes 160 (or 2 bipolar electrodes), two on either face of the electrode carrier 157. A non-conductive insulator 180 divides the electrode carrier 157 into the bipolar electrodes 160.

In one embodiment, the fabric is formed from a composite yarn with a thermoplastic elastomer (TPE) core and multiple polyfilament nylon bundles wound around the TPE as a cover. The nylon bundles are plated with thin conductive metal layers. Preferably, the nylon is metallized, but not the TPE core. This construction facilitates stretching; the nylon windings open up their coils as the TPE core is elongated, without cracking the metallic layer. The TPE core facilitates recovery from the stretched position, pulling the nylon coils back into their initial configuration.

In an alternative embodiment, the electrode carrier 157 can be a sack formed of a material that is non-conductive, that is permeable to moisture, and that can be compressed to a smaller volume and subsequently released to its natural size upon elimination of compression. Examples of materials for the electrode carrier 157 include foam, cotton, fabric, or cotton-like material, or any other material having the desired characteristics. The electrodes 160 can be attached to the outer surface of the electrode carrier 157, e.g., by deposition or another attachment mechanism. The electrodes 160 can be made of lengths of silver, gold, platinum, or any other conductive material. The electrodes 160 can be formed on the electrode carrier 157 by electron beam deposition, or they can be formed into coiled wires and bonded to the electrode carrier 157 using a flexible adhesive. Other means of attaching the electrodes, such as sewing them onto the surface of the electrode carrier 157, may alternatively be used.

Referring again to FIGS. 5B and 5C, an introducer sheath 182 facilitates insertion of the ablation device 150 into, and removal of the device from, the uterine cavity 100. The sheath 182 is a tubular member that is slidable over the shaft 158. The sheath 182 is slidable between a distal condition, shown in FIG. 5B, in which the RF applicator head 152 is compressed inside the sheath, and a proximal condition in which the sheath 182 is moved proximally to release the RF applicator head 152 from inside the sheath 182 (FIG. 5A). By compressing the electrode carrier 157 to a small volume, the RF applicator head 152 can be easily inserted transcervically into the uterine cavity 100.

During use, the sheath 182 is retracted from the electrode carrier 157, for example, by moving a distal handle member toward a proximal handle member to slide the sheath 182 in the distal direction. Moving the distal handle member toward the proximal handle member can also advance the shaft 158 in the proximal direction. The movement of the shaft 158 relative to the suction/insufflation tube causes the shaft 158 to pull proximally on the flexible member 176. Proximal movement of the flexible member 176 in turn pulls the flexure 178, causing it to move to the opened condition shown in FIG. 5C (see also FIG. 6B). In one embodiment, a locking mechanism (not shown) is required to hold the shaft in the fully withdrawn condition to prevent inadvertent closure of the RF applicator head 152 during the ablation procedure.

The amount by which the flexible member 176 is deformed outwardly from the tube 162 can be controlled by manipulating the handle 156 to slide the shaft 158, proximally or distally. The amount by which the shaft 158 is slid relative to the tube 162 controls the shape of the flexible member 176.

As mentioned above, in an alternative embodiment, the handle 156 can be configured so that the tube 162 can be moved distally relative to the shaft 158. Distal movement of the tube 162 in turn deforms the flexible member 176 outwardly. The amount by which the flexible member 176 is deformed outwardly from the tube 162 can be controlled by manipulating the handle 156 to slide the tube 162 proximally or distally, and the amount by which the tube 162 moves relative to the shaft 158 controls the shape of the flexible member 176.

As shown in FIG. 5B, a flow pathway 186 is formed from the RF applicator head 152 to the suction/insufflation port 188. The proximal end of the suction/insufflation tube 162 is fluidly coupled to the flow pathway so that gas fluid may be introduced into, or withdrawn from the suction/insufflation tube 162 via the suction/insufflation port 188. For example, suction may be applied to the fluid port 188 using a suction/insufflation unit 190. This causes water vapor within the uterine cavity 100 to pass through the permeable electrode carrier 157, into the suction/insufflation tube 162 via holes 162a, through the tube 162, and through the suction/insufflation unit 190 via the port 188. If insufflation of the uterine cavity 100 is desired, insufflation gas, such as carbon dioxide, may be introduced into the suction/insufflation tube 162 via the port 188. The insufflation gas travels through the tube 162, through the holes 162a, and into the uterine cavity 100 through the permeable electrode carrying member 157.

Figure 6E:
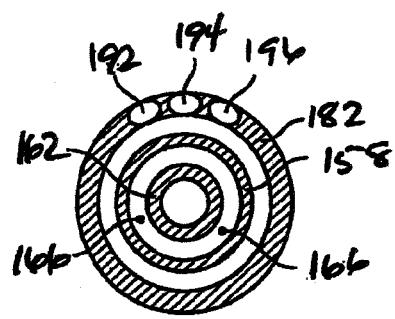
FIG. 6E is a cross-sectional view of a main body of the tubal occlusion device of FIGS. 5A-C.

One or more additional components can be provided for endoscopic visualization purposes. For example, lumens 192, 194, and 196 may be formed in the walls of the introducer sheath 182 as shown in FIG. 6E. An optical instrument can be used to provide images from within the uterine cavity. For example, referring to FIGS. 5C and 6E, an imaging conduit, such as a fiberoptic bundle, extends through lumen 192 and is coupled via a camera cable 193 to a camera 195. Images taken from the camera may be displayed on a monitor 197. An illumination fiber 198 can extend through lumen 194 and couple to an illumination source 199. The optional third lumen 196 can be an instrument channel through which surgical instruments may be introduced into the uterine cavity 100, if necessary. In an alternative embodiment, one or more of the lumens 192, 194, 196 can be formed in the walls of the shaft 158.

Because during use it is most desirable for the electrodes 160 on the surface of the electrode carrier 157 to be held in contact with the interior surface of the uterine cavity 100 and tubal ostia 110, the electrode carrier 157 may have additional components inside it that add structural integrity to the electrode carrying means when it is deployed within the body.

Figure 7:
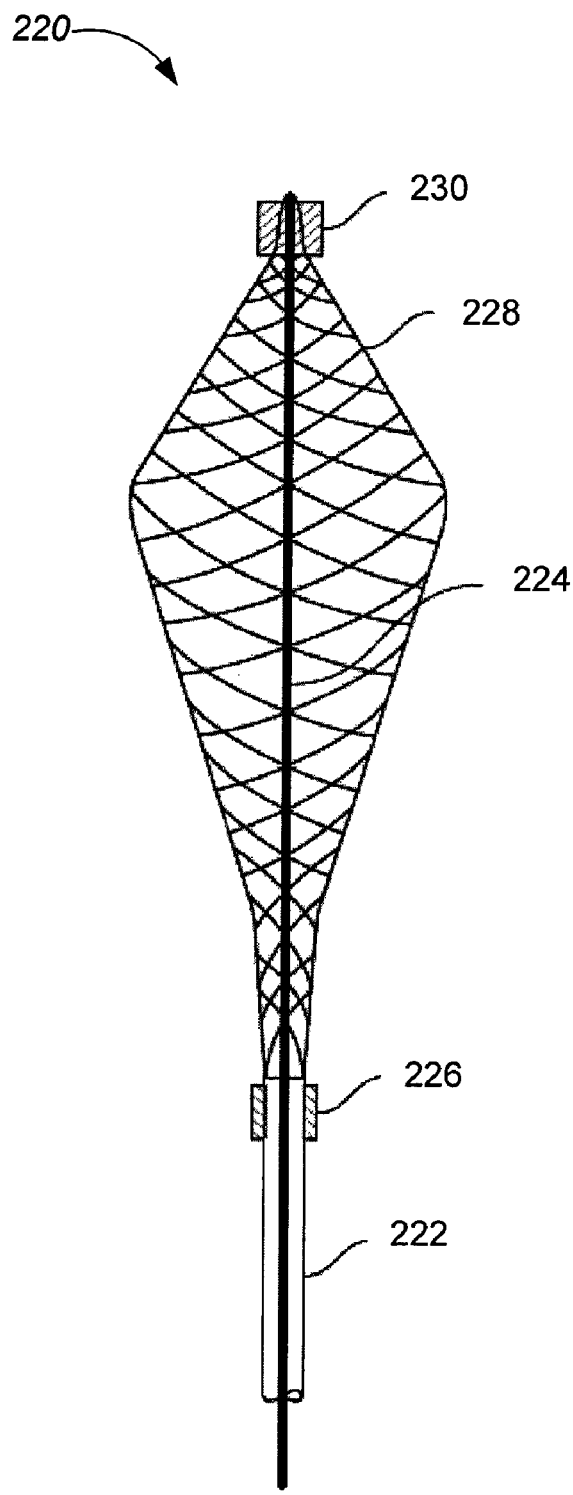
FIG. 7 is a schematic representation of an alternative embodiment of a structural body of an RF applicator head.

Referring to FIG. 7, an alternative embodiment of a structural body 220 of the RF applicator head 152 is shown. The structural body 220 includes an external hypotube 222 and an internal hypotube 224. If implementing the structural body 220 in the embodiment of the ablation device 150 described above, the external hypotube 222 can be the shaft 158 and the internal hypotube 224 can be the suction/insufflation tube 162. A cage 228 is formed over the internal hypotube 224 configured in a V-shape at the distal end 230 that can reach into a tubal ostium 110. The cage 228 can be a braided or woven structure made from a memory material, e.g., Nitinol.

The cage 228 can be collapsed into a narrow cylindrical configuration by moving the internal hypotube 224 relative to the external hypotube 222, e.g., by pushing the internal hypotube 224 distally away from the external hypotube 222. In a collapsed state the cage 228 can fit, for example, within the sheath 182 described above, when the RF applicator head 152 is placed in a closed position. Once the sheath 182 is removed and the internal hypotube 224 is moved back into the open position relative to the external hypotube 222, the nature of the material from which the cage 228 is made expands the cage 228 into the desired shape that is depicted. An electrode carrier, such as the electrode carrier 157 made from a metallized fabric described above, can be fitted over the structural body 220, completing the RF applicator head.

Example Device #2

Figure 8A:
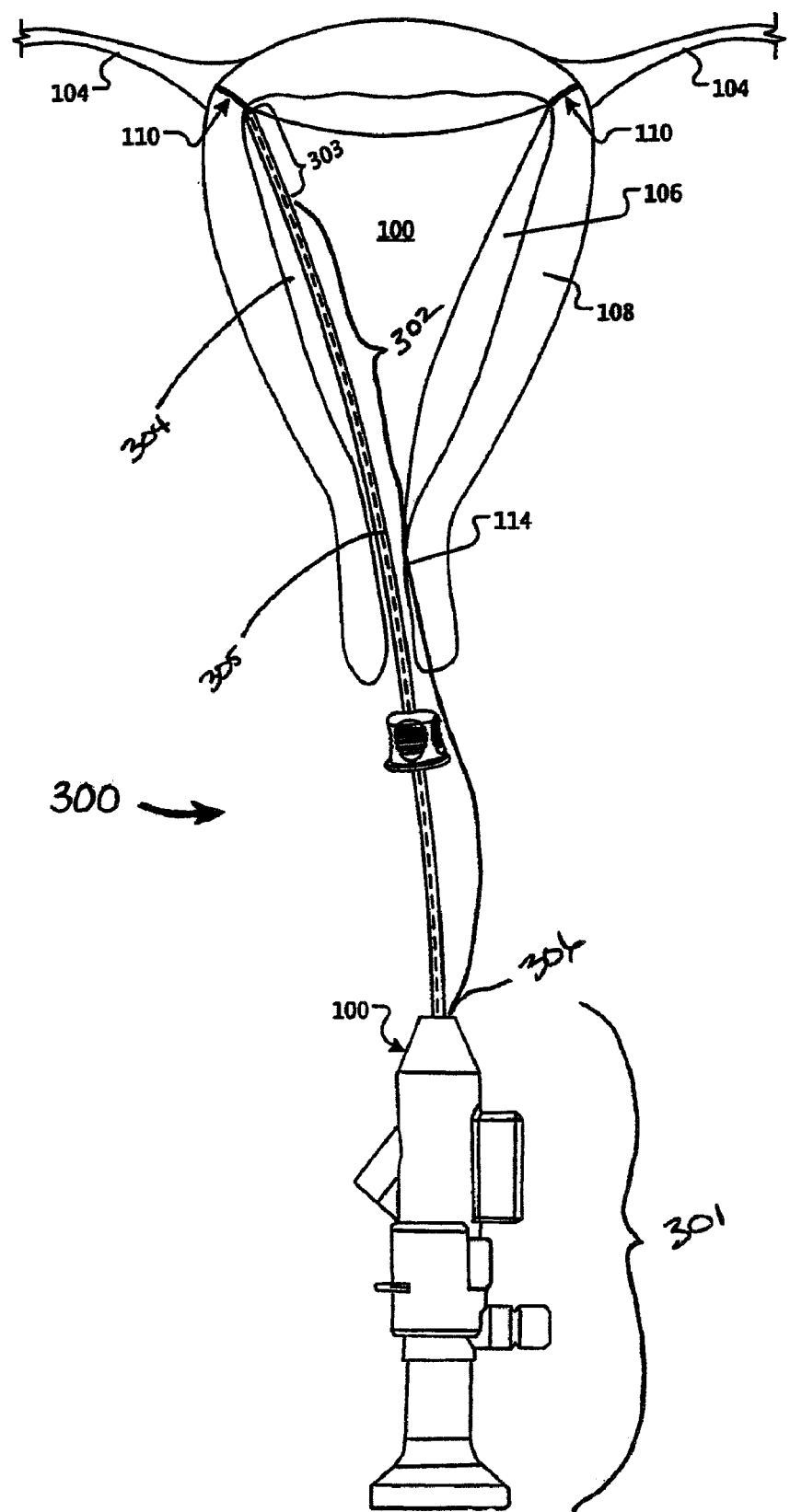
FIG. 8A shows an alternative embodiment of a tubal occlusion device positioned in a uterus.

Referring to FIG. 8A, a schematic representation of an alternative embodiment of an ablation device 300 is shown, which is described further in U.S. patent application Ser. No. 11/532,886, entitled "Curved Endoscopic Medical Device", filed by Hilario et al, on Sep. 18, 2006, the entire contents of which are hereby incorporated by reference herein. The ablation device 300 generally includes three major components: a handle 301, a curved shaft 302, and a radio frequency (RF) applicator head 303. The curved shaft 302 includes a distal end 304, a proximal end 306, and a hollow central interior 305. The curved shaft 302 is a substantially rigid member configured with a curve to facilitate the advancement of the distal end 304 through a body cavity to a region of tissue to be ablated. The central interior 305 includes one or more lumens. For example, the central interior 305 can include a lumen that can be operated so as to couple a vacuum source to the RF applicator head 303 positioned at the distal end 304 of the elongate member 320. The vacuum can be used to draw moisture away from one or more electrodes that can comprise at least a portion of the RF applicator head 303. Additionally, a lumen (either the same lumen that couples to a vacuum source or a different lumen) can be configured to receive a curved hysteroscope. The ablation device 300 is configured to facilitate entry into a uterine cavity to perform a tubal occlusion procedure.

The RF applicator head 303 is positioned at the distal end 304 of the curved shaft 302 and includes an electrode carrier having one or more bipolar electrodes. One or more electrical conductors extend from the RF applicator head 303 to the proximal end 306 of the curved shaft 302 and electrically couple the RF applicator head 303 to a controller. The controller can be operated so as to control the delivery of RF energy to the one or more bipolar electrodes.

Figure 8B:
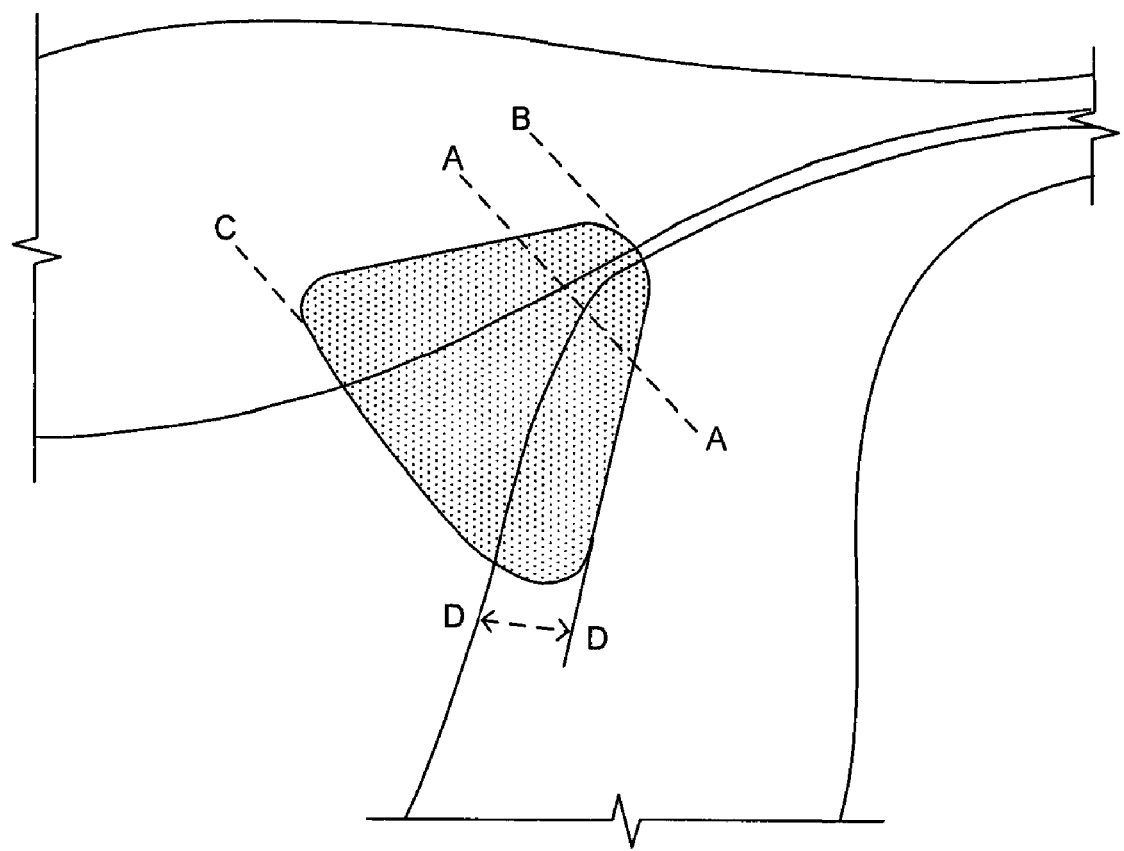
FIG. 8B is a schematic representation of a region of ablated tissue in a uterus and tubal ostium.

The RF applicator head 303 is introduced transcervically into the uterine cavity and positioned at a tubal ostium 110. Transmitting RF energy through the RF applicator head 303 ablates the uterine tissue 106, 108 and the tissue within the tubal ostium 110. Following the destruction of the tissue at the tubal ostium 110, the healing response occludes the tubal ostium 110 and the adjacent portion of the fallopian tube 104 resulting in sterilization. Referring to FIG. 8B, the targeted tissue destruction from A-A to B is approximately 1.5 to 2.5 millimeters, from A-A to C is approximately 10 to 20 millimeters and the depth D-D is typically approximately 2.0 to 3.5 millimeters.

Figure 9:
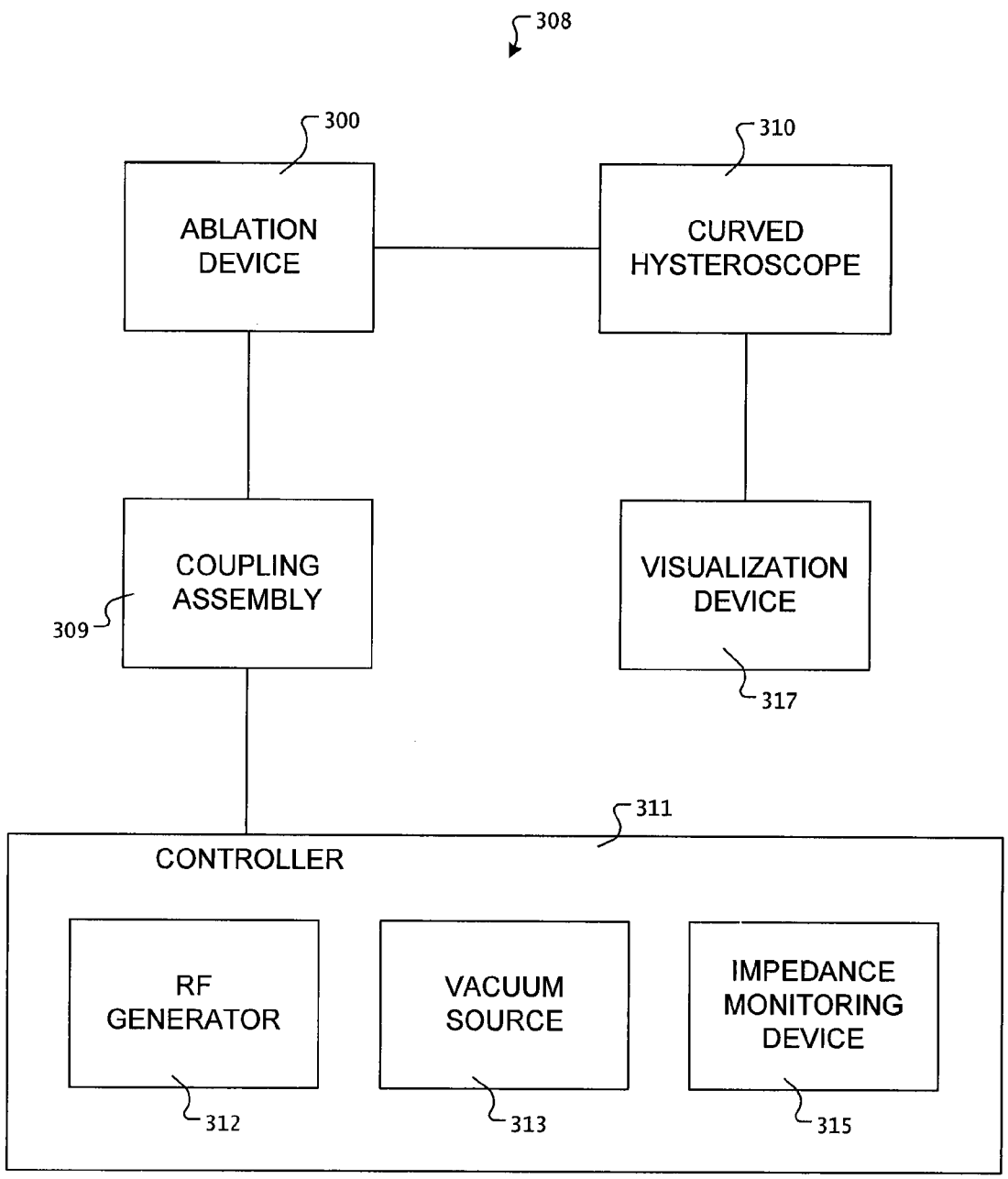
FIG. 9 is a schematic block diagram of a system for tubal occlusion.

Referring to FIG. 9, a schematic block diagram is shown of a system 308 for tissue ablation using the ablation device 300. The system 308 includes the ablation device 300 that is coupled to a coupling assembly 309 and configured to receive the curved hysteroscope 310. The coupling assembly 309 couples the ablation device 300 to a controller 311. The controller 311 includes an RF generator 312 and a vacuum source 313. Optionally, the controller 311 can include an impedance monitoring device 315. In one implementation, the controller 311 is a single device, however, in other implementations, the controller 311 can be formed from multiple devices coupled to one another.

Referring to FIGS. 10A-10E, one implementation of a coupling assembly 309 is shown connected to the ablation device 300 shown in FIG. 8A. Other configurations of the coupling assembly 309 are possible, and the one described herein is just one example for illustrative purposes. The coupling assembly 309 as well as certain aspects of the ablation device 300 shall be described in further detail below in reference to FIGS. 10A-E.

Figure 10A:
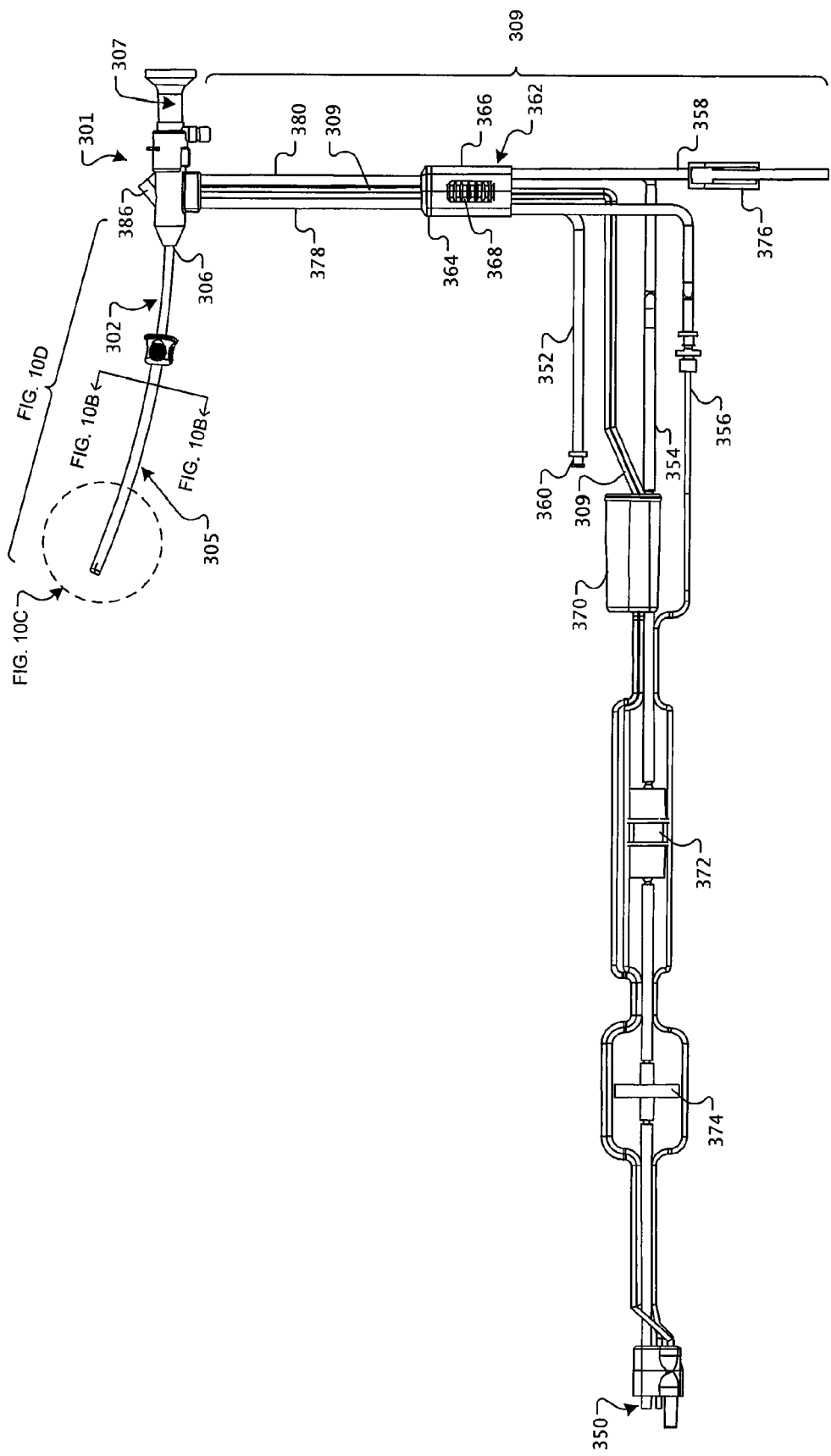
FIG. 10A shows the tubal occlusion device of FIG. 8A connected to a coupling assembly.
Figure 10D:
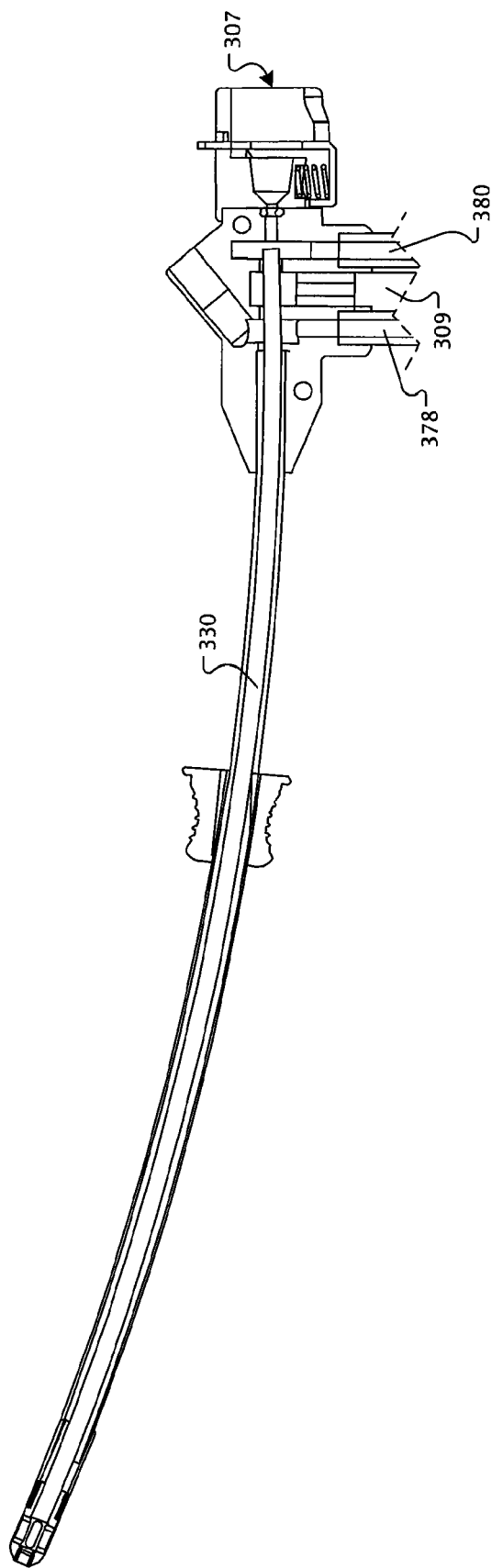
FIG. 10D is a cross-sectional view of the tubal occlusion device shown in FIG. 8A.

Referring particularly to FIGS. 10B-D, a cross-sectional side view of the ablation device 300 is shown (FIG. 10D), as well as the distal ends of connectors of the coupling assembly 309. In particular, in this implementation, there are at least three connections made to the coupling assembly 309. A first connection connects the ablation device 300 to a vacuum feedback/saline supply line 378. A second connection connects the ablation device 300 to an RF cable bundle 309. A third connection connects the ablation device 300 to a suction/waste line 380.

The vacuum feedback/saline supply line 378 fluidly couples to an outer lumen 322 formed in the curved shaft 302, shown in the cutaway view in FIG. 10B. As described further below, saline can be supplied to the distal end of the ablation device 300 and into the uterine cavity to distend the cavity during a medical procedure. The RF cable bundle 309 is electrically connected to connectors 332 that run from the RF applicator head 303 to the proximal end of the ablation device 300, and provides RF power to the one or more bipolar electrodes, as described further below. The suction/waste line 380 is fluidly coupled to an inner lumen 330 included in the curved shaft 302, and provides suction to the RF applicator head to maintain the one or more bipolar electrodes in contact with surrounding tissue as well as removing liquid and liberated steam during an ablation procedure. The connectors 332 can be conductive elements formed on the outer surface of an insulating tube that provides the inner lumen 330. The proximal end of the ablation device 300 includes a port 307 configured to receive the hysteroscope 310 into the inner lumen 330 of the ablation device 300.

Referring to FIG. 10C, a cross-sectional side view of the RF applicator head 303 is shown. The inner lumen 330 in the curved shaft 302 extends through the RF applicator head 303 to the distal tip 326. When the hysteroscope 310 is positioned within the inner lumen 330, a distal end of the hysteroscope 310 sits just proximal the distal tip 326 of the ablation device 300, providing for visualization from the distal tip 326 of the device 300.

Figure 10E:
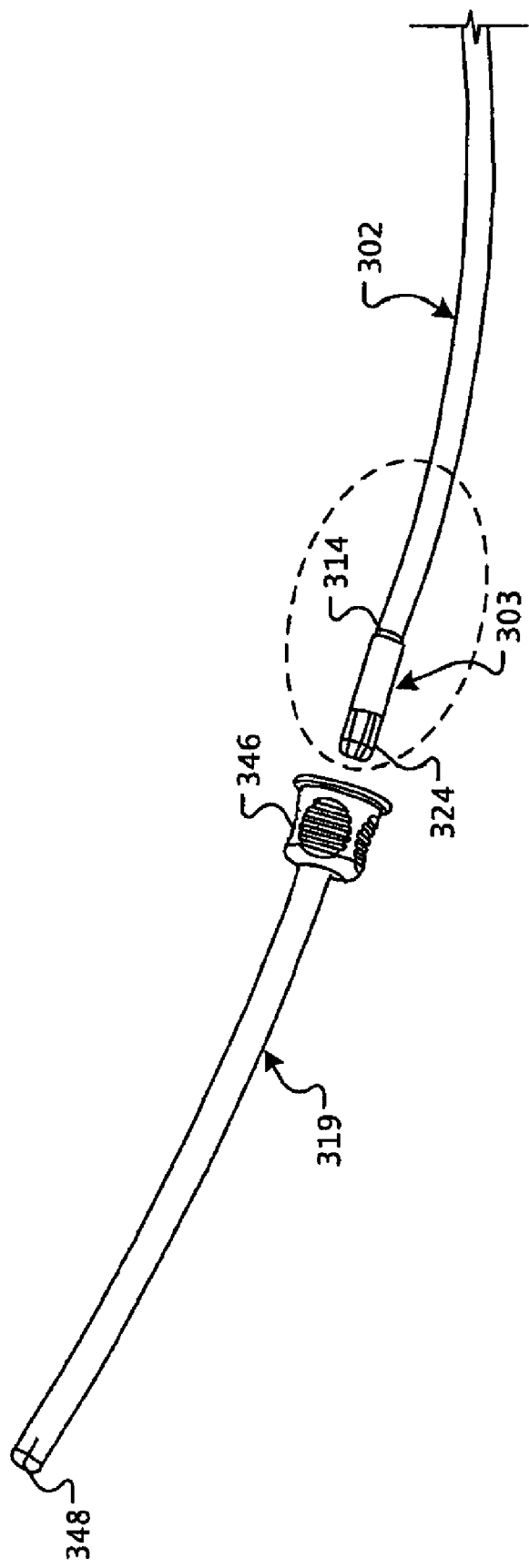
FIG. 10E shows an exploded view of a sheath and a distal component of the ablation device shown in FIG. 8A.

Referring to FIG. 10E, a protective sheath 319 facilitates insertion of the ablation device 300 into, and removal of the ablation device 300 from, the uterine cavity 100. The protective sheath 319 is a tubular member that is slidable over the curved shaft 302 and includes a collar 346 and an expandable tip 348. The protective sheath 319 is slidable between a distal condition, shown in FIG. 10A, in which the RF applicator head 303 is inside the sheath, and a proximal condition in which the protective sheath 319 is moved toward the proximal end of the curved shaft 302. The expandable tip 348 opens so as to release the RF applicator head 303 from inside the protective sheath 319. By inserting the RF applicator head 303 into protective sheath 319, the RF applicator head 303 can be easily inserted transcervically into the uterine cavity 100.

During use, the protective sheath 319 is retracted from the RF applicator head 303, for example, by grasping the collar 346 and moving the protective sheath 319 toward the proximal end of the curved shaft 302. Alternatively, moving the handle 301 toward the collar 346 can also advance the curved shaft 302 relative to the sheath 319, thereby exposing the RF applicator head 303.

Figure 11A:
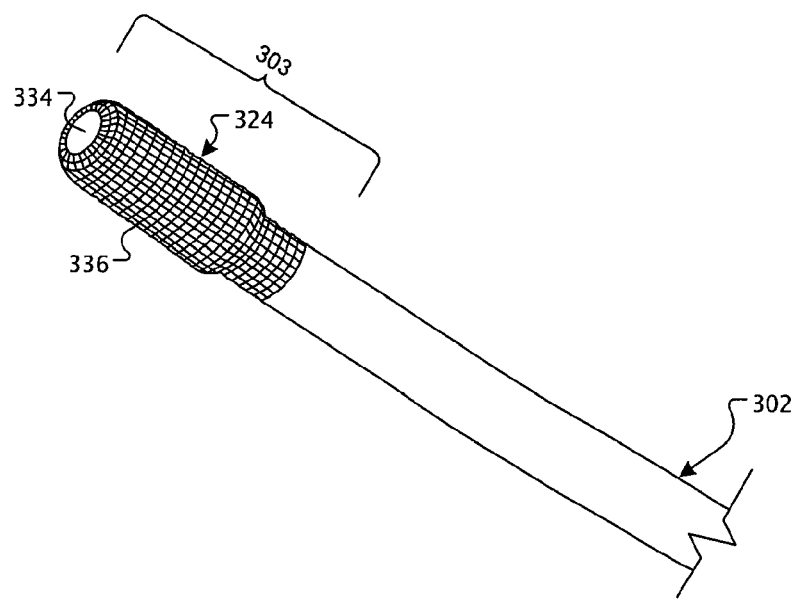
FIG. 11A shows an RF applicator head.
Figure 11B:
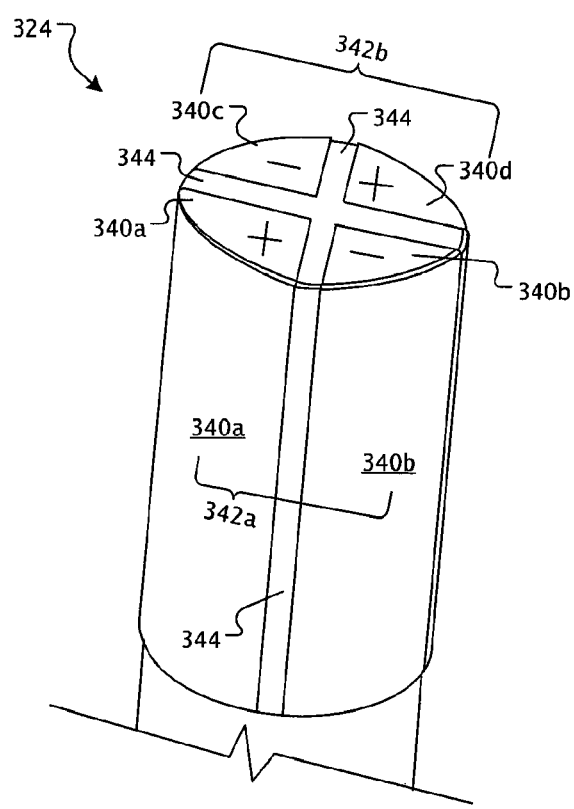
FIG. 11B shows a schematic representation of an electrode carrier.

Referring to FIG. 11A, a close up view of the RF applicator head 303 is shown including an electrode carrier 324. FIG. 11B shows a schematic representation of the electrode carrier 324 including conductive regions forming bipolar electrodes 342a and 342b and non-conductive regions 344 providing insulation therebetween. In the current embodiment, the electrode carrier 324 includes an approximately cylindrically shaped support member within a fabric sheath 336. The fabric sheath 336 includes conductive metallized regions 340a-d separated by a non-conductive region 344 formed onto the fabric sheath 336. A pair of electrodes, i.e., one positively charged and the other negatively charged, together form one bipolar electrode. In the embodiment shown, the electrode pair 340a and 340b together form a bipolar electrode 342a, and the electrode pair 340c and 340d together from a bipolar electrode 342b. In one implementation, the electrode carrier 324 has a diameter in the range of approximately five to ten millimeters, for example, six millimeters. However, it should be noted that other sizes and configurations are possible. For example, the electrode carrier can be an approximately tapered cylindrical support member within a fabric sheath.

In another implementation, the electrode carrier 324 can be formed from a metallic mesh insert molded into a support member formed from a plastic material. The metallic mesh insert forms the electrically conductive regions (i.e., electrodes 340a-d) and the plastic material forms the non-conductive regions (i.e., insulator 344) thereby creating the one or more bipolar electrodes (i.e., bi-polar electrodes 342a and 342b). The metallic mesh insert can be formed from an electrically conductive material such as a stainless steel material, a platinum material, or other electrically conductive materials.

Referring again to the embodiment of the electrode carrier 324 formed from a fabric sheath 336 stretched over a support member, in one implementation, the fabric sheath 336 is formed from a nylon mesh, and the conductive metallized regions are formed by coating the nylon mesh with gold. In one embodiment, the fabric sheath 336 is formed from a composite yarn with a thermoplastic elastomer (TPE) core and multiple polyfilament nylon bundles wound around the TPE as a cover. The nylon bundles are plated with thin conductive metal layers. Preferably, the nylon is metallized, but not the TPE core. In another embodiment, nylon filaments are coated with a silver and/or gold coating. The filaments are sewn or knitted together with a non-conductive nylon or spandex filament to form the bipolar fabric sheath.

Figure 12:
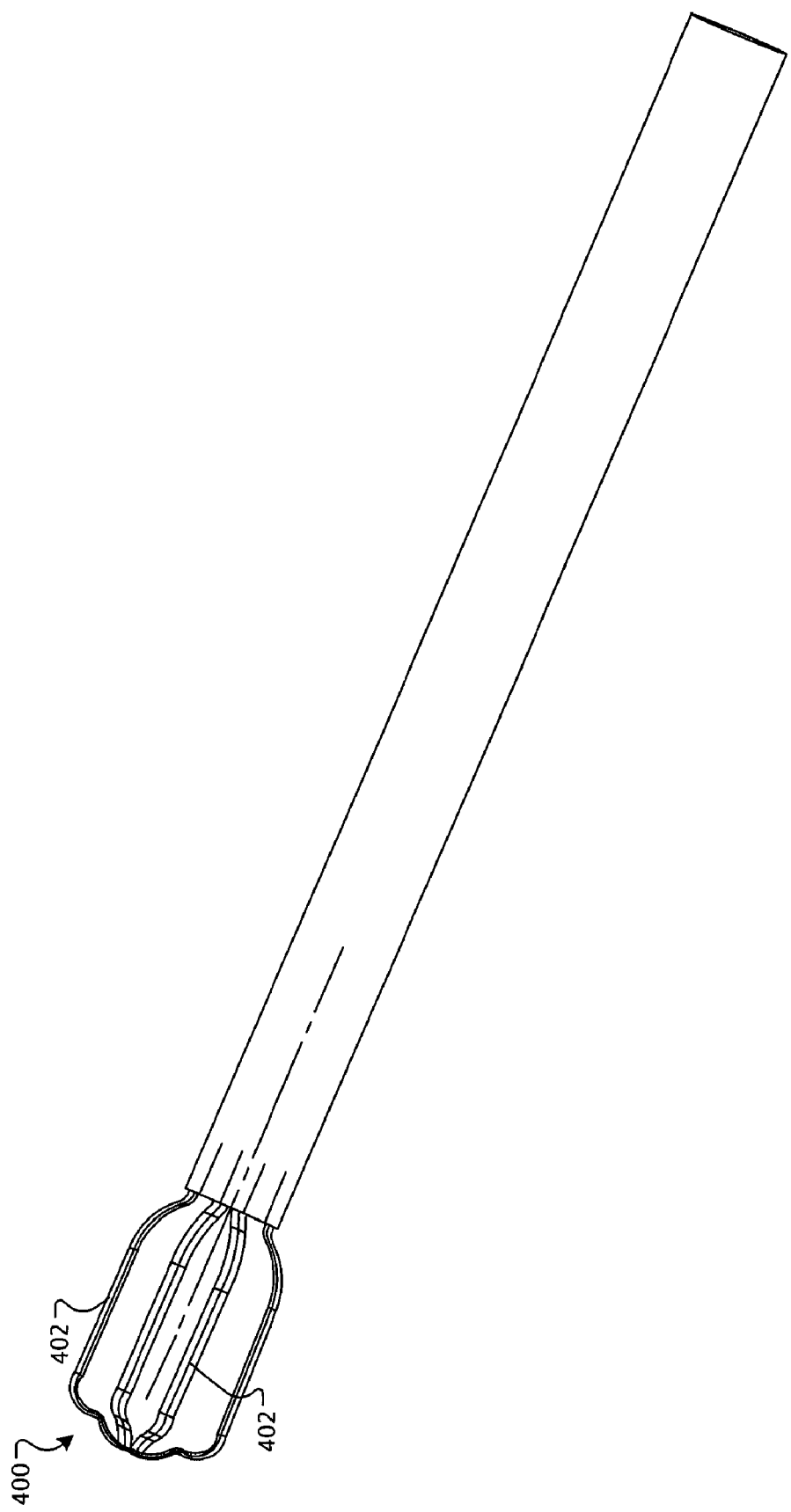
FIG. 12 shows an alternative RF applicator head.

In another embodiment, the electrode carrier can be placed over an expandable or self-expandable support member. Referring to FIG. 12, the support member 400 can have a series of expandable arms 402 that when housed in an outer sheath are in a collapsed state. Once the device is inserted into the uterine cavity, the outer sheath can be withdrawn to expose the electrode array and allow the support member arms to expand. This can be advantageous to have a smaller diameter insertion profile and allow increased electrode spacing, thereby generating a deeper ablation profile. In one implementation, the support member can be fabricated from Nitinol, Elgiloy or another shape memory alloy.

The support member included in the electrode carrier 324 can be formed from any suitable material, one example being Ultem®, a thermoplastic PolyEtherlmide (PEI) that combines high strength and rigidity at elevated temperatures with long term heat resistance (Ultem is a registered trademark of General Electric Company Corporation of New York, N.Y.).

In an alternative embodiment, the electrode carrier 324 can be a sack formed of a material that is non-conductive, and that is permeable to moisture. Examples of materials for the electrode carrier 324 include foam, cotton, fabric, or cotton-like material, or any other material having the desired characteristics. The electrodes 340a-d can be attached to the outer surface of the electrode carrier 324, e.g., by deposition or another attachment mechanism. The electrodes 340a-d can be made of lengths of silver, gold, platinum, or any other conductive material. The electrodes 340a-d can be formed on the electrode carrier 324 by electron beam deposition, or they can be formed into coiled wires and bonded to the electrode carrier 324 using a flexible adhesive. Other means of attaching the electrodes 340a-d, such as sewing them onto the surface of the electrode carrier 324, may alternatively be used.

Referring again to FIG. 10A, the coupling assembly 309 shall be described in further detail. The RF cable bundle 309 includes one or more electrical conductors (i.e., wire, flexible circuit, stripline, or other) that electrically connect to the electrical conductors 332 included in the ablation device 300. The RF cable bundle 309 connects at the distal end 350 of the coupling assembly 309 to the controller 311, which is configured to control the delivery of radio frequency energy to the RF applicator head 303.

The coupling assembly 309 further includes a saline supply line 352 and a vacuum feedback line 356 that merge proximal to a fluid control switch 362 to form the vacuum feedback/saline supply line 378. The vacuum feedback/saline supply line 378 is coupled to the outer lumen 322 included in the curved shaft 302 of the ablation device 300. The controller 311 is in communication with and receives a vacuum feedback signal from the vacuum feedback line 356. The vacuum feedback line 356 allows the controller 311 to monitor the vacuum level at the ablation site. The saline supply line 352 includes a connector 360 (e.g., female luer, threaded connection, or other) located on the distal end of the saline supply line 352. The connector 360 can be removably coupled to a saline supply source (i.e., intravenous bag, or other). The fluid control switch 362 can control the flow of fluid (i.e., saline) to the ablation site and, in one embodiment, includes a roller clamp body top half 364, a roller clamp body bottom half 366, and a roller wheel 368.

The coupling assembly 309 further includes a waste line 358 and suction line 354. The suction line 354 and the waste line 358 merge proximal to the fluid control switch 362 to form the suction/waste line 380. The suction/waste line 380 is coupled to the inner lumen 330 included in the curved shaft 302 of the ablation device 300.

The suction/waste line 380 couples to a vacuum source 313 (FIG. 9). The vacuum source 313 can be operated by the controller 311 to draw the tissue surrounding the electrode carrier 324 into contact with the one or more bipolar electrodes 342a-b. Additionally, the vacuum source 313 can draw the moisture that can be generated during the delivery of the radio frequency energy to the one or more bipolar electrodes 342a-b away from the one or more bipolar electrodes 342a-b. Further, the vacuum source 313 can substantially eliminate the liquid surrounding the one or more bipolar electrodes 342a-b. The moisture is drawn by the vacuum source 313 through the inner lumen 330, to the suction/waste line 380 and removed via the waste line 358. The waste line 358 can include a waste line roller clamp 376 that can be used to control the flow of waste, fluid, or both that is removed by the ablation device 300 from the tissue ablation site. The vacuum relief valve 386 included in the handle 301 of the ablation device 300 is in fluid communication with the suction/waste line 380 and can aid in relieving excess vacuum.

The suction line 354 can include a suction canister 370, a desiccant 372, and a filter 374. The suction canister 370 can operate as a reserve and be used to smooth out the level of vacuum applied to the ablation site. The desiccant 372 can serve to substantially dry out or absorb at least a portion of the moisture that can be contained in the fluid evacuated from the ablation site by the vacuum source 313. The filter 374 can serve to prevent any particulate matter evacuated from the ablation site by the vacuum source 313 from being communicated to the controller 311, the vacuum source 313, or both.

A hysteroscope 310 is configured to position within the inner lumen 330 of the curved shaft 302. In one embodiment, the hysteroscope 310 is substantially rigid and is configured with a curve that is substantially similar to the curve of the curved shaft 302. The curved hysteroscope 310 can be formed including optics similar to a conventional straight hysteroscope, that is, the scope can have a conventional lens system including an objective lens and a series of relay and filed lenses, to transfer the image to the camera focal plane. The relay and field lenses can be fabricated from glass elements in a typical fashion (e.g., ground and polished) and assembled with a series of spacers. The advantage of such a device is the high resolution. In another embodiment, the shaft 302 is not flexible and takes on the curve of the hysteroscope 310 upon positioning the hysteroscope 310 therein.

In yet another embodiment, the hysteroscope 310 is flexible and can flex to accommodate the curve of the curved shaft 302. In this configuration, the scope has an objective lens coupled to an image guide, e.g., a coherent bundle of fibers. The objective lens images the object to the distal end of the image guide. The individual fibers transfer the image to the proximal surface of the image guide. Additional optics are used to transfer the image to either the user's eye or the camera focal plane. The advantage of this type of scope is the scope's flexibility and ability to fabricate small diameter devices.

The hysteroscope 310 generally has an optical system that is typically connected to a video system and a light delivery system. The light delivery system is used to illuminate the target site under inspection. Referring again to the system 308 shown in FIG. 9, the hysteroscope 310 can be coupled to an external visualization device 317, for example, a monitor, to provide viewing by the operator. In some embodiments, the light source is outside of the patient's body and is directed to the target site under inspection by an optical fiber system. The optical system can include a lens system, a fiberscope system, or both that can be used to transmit the image of the organ to the viewer.

In one implementation, the ablation device 300 shown in FIG. 8A can have a curved shaft 302 that is approximately 30 centimeters long and a cross-sectional diameter of approximately 4 millimeters. The curved shaft 302 can be formed from Stainless Steel 300 series, Nitinol, Elgiloy or other metals and the handle 301 can be formed from plastic or metal, including Stainless Steel 300 series, ABS plastic, Ultem, polycarbonate, Styrenes or other machinable or moldable plastics. The sheath 319 can be formed from PET, TFE, PTFE, FEP, or polyolefin. Components of the coupling assembly 309 can be formed from Tygon tubing and/or PVC tubing.

In one embodiment, ramping up the RF power density includes steadily or gradually increasing the current over a second time period after an initial time period. Determining when to begin the power ramp-up, i.e., determining the value of the initial time period, and the amount by which to ramp-up, in one implementation is according to a time-based function and in another implementation is according to an impedance-based function.

As discussed above, in an alternative embodiment the curved endoscopic device can be configured as a curved endoscope that includes a working channel to receive a tool for performing a medical procedure. For illustrative purposes, referring to the ablation device 300, an alternative configuration would include a curved hysteroscope with a working channel configured to receive an ablation device similar to the ablation device 300, i.e., the reverse of the ablation device 300, which includes an inner lumen 330 to receive a hysteroscope. In other implementations, the curved endoscopic device can be configured as a curved endoscope adapted to be received by a body cavity other than a uterus, for example, by a nasal passage. The working channel can be adapted to receive a tool other than an ablation device, depending on the medical procedure to be performed within the nasal passage.

Example Device #3

Figure 13:
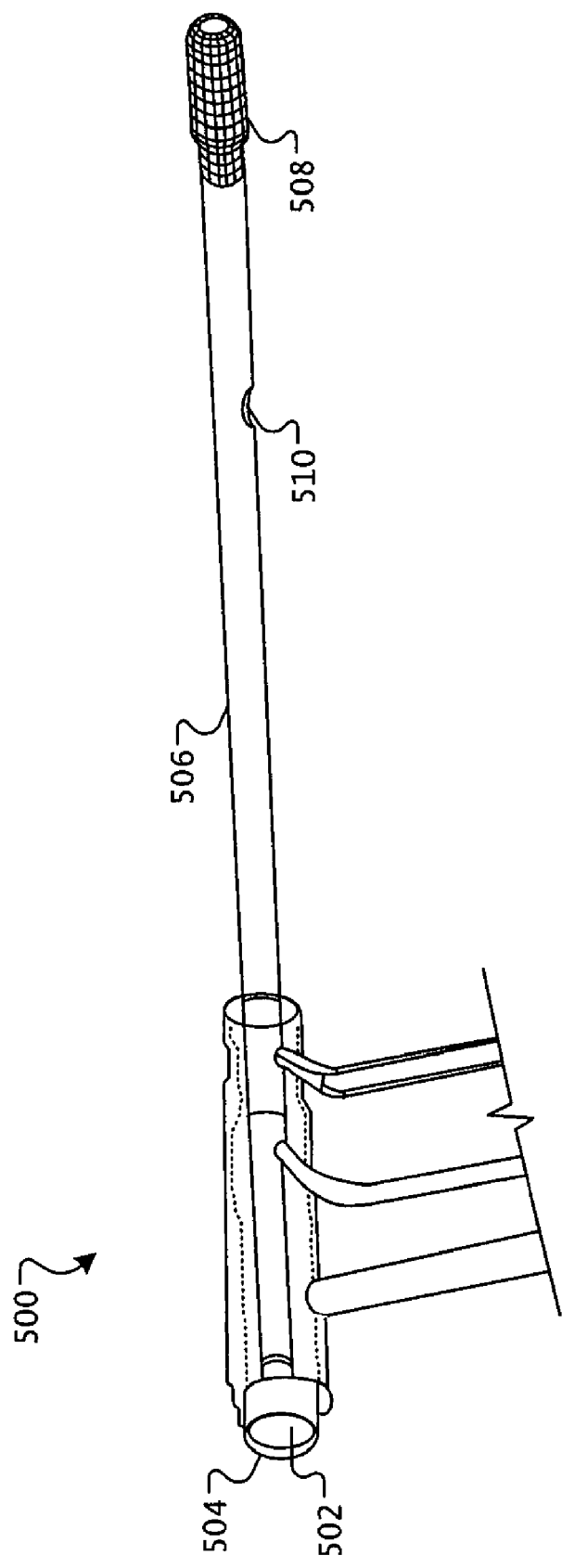
FIG. 13 shows an alternative embodiment of a tubal occlusion device.

Referring to FIG. 13, an alternative embodiment of an ablation device 500 is shown. The ablation device 500 includes a port 502 configured to receive an endoscope and a mating connector 504 configured to mate with and connect to the endoscope. The port 502 is connected to a lumen formed within a shaft 506. An electrode carrier 508 is positioned at the distal end of the shaft 506. The shaft 506 of the ablation device 500 includes a side hole 510 that is proximal to the electrode carrier 508. An endoscope can be inserted into the port 502 and advanced along the length of the inner lumen toward the side hole 510 formed in the shaft 506. The distal end of the endoscope can be passed through the side hole 510 to provide the endoscope with an orientation whereby the distal end of the endoscope is substantially parallel to the shaft 506 of the ablation device 500. The shaft 506 is flexible, and can be formed from a polymer. The action of inserting a rigid endoscope into the lumen formed in the shaft 506 curves the shaft 506 at its distal end, deflecting the distal tip of the ablation device in a direction opposite the endoscope position. That is, the shaft 506 can be flexible but elastic with restorative forces to urge the shaft 506 to a shape that is substantially straight.

The distal end of the endoscope includes optics (e.g., lens, fiber optics, or other) to provide visualization when positioning the electrode carrier 508 at an ablation side. The side-by-side configuration of the endoscope optics and the electrode carrier 508 can provide the user with off-axis viewing. For example, the endoscope can have off-axis viewing in the range of ten degrees to ninety degrees, and such off-axis viewing can help the user to align the electrode carrier 508 with an ablation sight, for example, the tubal ostium of a fallopian tube.

The ablation device 500 can be configured to mate with a coupling assembly similar to the coupling assembly described in reference to FIG. 10A, or a differently configured coupling assembly, which couples the ablation device 500 to a controller including or connected to an RF generator, vacuum source and optionally an impedance monitoring device. In another embodiment, the ablation device 500 can be configured with a curve, for example, in one implementation a curve to facilitate insertion into the uterine cavity 100 or another body cavity.

Depth of Destruction

When performing the permanent tubal occlusion, for example, using one of the example embodiments of an ablation device described above, the depth of destruction of the target tissue can be controlled to achieve repeatable, predetermined depths. Variables such as the electrode construction, power applied to the electrodes (power density or power per unit surface area of the electrode), and the tissue impedance at which power is terminated can be used to affect the depth of tissue destruction, as discussed further below.

The spacing between the electrodes (i.e., the distance between the centers of adjacent electrodes) and the widths of the electrodes can be selected so that ablation will reach predetermined depths within the tissue, particularly when maximum power is delivered through the electrodes. Maximum power is the level at which low impedance, low voltage ablation can be achieved. The depth of ablation is also affected by the electrode density (i.e., the percentage of the target tissue area which is in contact with active electrode surfaces) and may be regulated by pre-selecting the amount of active electrode coverage. For example, the depth of ablation is much greater when the active electrode surface covers more than 10% of the target tissue than it is when the active electrode surfaces covers only 1% of the target tissue.

By way of illustration, using 3-6 mm spacing, an electrode width of approximately 0.5-2.5 mm and a delivery of approximately 20-40 watts over a 9-16 cm$^2$ target tissue area, will cause ablation to a depth of approximately 5-7 millimeters when the active electrode surface covers more than 10% of the target tissue area. After reaching this ablation depth, the impedance of the tissue will become so great that ablation will self-terminate. By contrast, using the same power, spacing, electrode width, and RF frequency will produce an ablation depth of only 2-3 mm when the active electrode surfaces covers less than 1% of the target tissue area.

Impedance Monitoring

When performing the permanent tubal occlusion, for example, using one of the example embodiments of an ablation device described above, to achieve the desired depth of ablation, the controller can be configured to monitor the impedance of the tissue at the distal end of the RF applicator head, for example, using an impedance monitoring device (e.g., the impedance monitoring device 315 shown in FIG. 9). The controller can include an automatic shut-off once a threshold impedance is detected. As the tissue is desiccated by the RF energy, fluid is lost and withdrawn from the region by a vacuum through the inner lumen and the suction/waste line. The suction draws moisture released by tissue undergoing ablation away from the electrode carrier and prevents formation of a low-impedance liquid layer around the electrodes during ablation. As more tissue is desiccated, the higher the impedance experienced at the electrodes. By calibrating the RF generator, taking into account system impedance (e.g., inductance in cabling etc.), a threshold impedance level can be set that corresponds to a desired depth of ablation.

Once the threshold impedance is detected, the controller shuts off the RF energy, preventing excess destruction of tissue. For example, when transmitting RF energy of 5 watts per square centimeter to tissue, an impedance of the tissue of 50 ohms can indicate a depth of destruction of approximately 3 to 4 millimeters at the proximal end and approximately 2.5 millimeters at the distal end. In an alternative embodiment, the RF generator can be configured such that above the threshold impedance level the RF generator's ability to deliver RF power is greatly reduced, which in effect automatically terminates energy delivery.

Power Ramping

In one implementation, when applying RF energy to perform the permanent tubal occlusion, a constant rate of RF power can be supplied for a first time period following which the RF power can be increased, either gradually or abruptly, for a second time period. Although the system can include a vacuum source to transport moisture away from the tissue site during ablation, after the first time period, the impedance at the RF applicator may decrease due to fluid migration into the site. Increasing the RF power at this point for the second time period can help to vaporize the excess fluid and increase the impedance. The RF power can be increased as described in U.S. patent application Ser. No. 11/532,889 entitled "Power Ramping During RF Ablation", filed Sep. 18, 2006, by Kotmel et al, the entire contents of which are hereby incorporated by reference herein.

A number of embodiments of the invention have been described. Nevertheless, it will be understood that various modifications may be made without departing from the spirit and scope of the invention. Accordingly, other embodiments are within the scope of the following claims.

What is claimed is:

1. A method for female sterilization comprising, for each fallopian tube:
    transcervically inserting and implanting a tubal occlusion device into the fallopian tube where the tubal occlusion device immediately occludes the fallopian tube;
    transcervically positioning a radio frequency (RF) applicator including one or more bipolar electrodes at a tubal ostium of the fallopian tube such that the one or more bipolar electrodes are positioned proximally relative to the implanted tubal occlusion device; and
    passing current through the RF applicator to destroy tissue to a known depth and to precipitate a healing response in surrounding tissue that over time scars, the scar tissue permanently occluding the fallopian tube;

wherein the tubal occlusion device remains in the fallopian tube after the RF applicator is removed from the respective fallopian tube and provides immediate and at least temporary sterilization before the scar tissue resulting from the application of current through the RF applicator is formed.

2. The method of claim 1, wherein the tubal occlusion device is formed at least partially from a biodegradable material and is configured to provide tubal occlusion for at least as long as a period of time required for the scar tissue to permanently occlude the fallopian tube.

3. The method of claim 1, wherein the tubal occlusion device is formed from a non-biodegradable material.

4. The method of claim 1, wherein the tubal occlusion device is configured as a screw and can be rotated within the tube upon insertion such that threads included on an exterior service of the tubal occlusion device are threaded into surrounding tissue providing a tight seal between the tubal occlusion device and the tissue.

5. The method of claim 1, wherein the tubal occlusion device is configured as a plug including one or more fixation elements configured to fixate onto surrounding tissue.

6. The method of claim 1, wherein the RF applicator comprises an RF applicator head including an electrode carrier with the one or more bipolar electrodes thereon and having an open and a closed position, the method further comprising:
  positioning the RF applicator such that a distal tip of the RF applicator head in a closed position advances into the tubal ostium;
  deploying the RF applicator head into an open position such that the RF applicator head approximates the shape of the uterine cavity in a region of the tubal ostium; and
  passing current through the one or more bipolar electrodes to the tubal ostium to destroy the tissue to a known depth.

7. The method of claim 1, further comprising:
  advancing an illuminator and an optical instrument into the uterine cavity; and
  wherein positioning the RF applicator head at the tubal ostium of a fallopian tube includes using the optical instrument to visualize the tubal ostium.

8. A method for fallopian tubal occlusion, comprising:
  transcervically inserting and implanting a tubal occlusion device into a fallopian tube where the tubal occlusion device occludes the fallopian tube;
  transcervically positioning a radio frequency (RF) applicator including one or more bipolar electrodes at a tubal ostium of the fallopian tube such that the one or more bipolar electrodes are positioned proximally relative to the implanted tubal occlusion device; and
  passing current through the RF applicator to destroy tissue to a known depth and to precipitate a healing response in surrounding tissue that over time scars, the scar tissue permanently occluding the fallopian tube;
  wherein, the tubal occlusion device is inserted into the fallopian tube first and the RF applicator is inserted second and, upon removal of the RF applicator, the tubal occlusion device inserted into the fallopian tube remains in the fallopian tube and provides immediate and at least temporary tubal occlusion before the scar tissue resulting from the application of current through the RF applicator is formed.

9. The method of claim 8, wherein the tubal occlusion device is formed at least partially from a biodegradable material and is configured to provide tubal occlusion for at least as long as a period of time required for the scar tissue to permanently occlude the fallopian tube.

10. The method of claim 9, wherein the tubal occlusion device is configured to provide tubal occlusion for at least three months from the date of insertion.

11. The method of claim 8, wherein the tubal occlusion device is formed from a non-biodegradable material.

12. The method of claim 8, wherein the tubal occlusion device is configured as a screw and can be rotated within the tube upon insertion such that threads included on an exterior surface of the tubal occlusion device are threaded into surrounding tissue providing a tight seal between the tubal occlusion device and the tissue.

13. The method of claim 8, wherein the tubal occlusion device is configured as a plug including one or more fixation elements configured to fixate into surrounding tissue.

14. The method of claim 8, wherein the RF applicator comprises an RF applicator head including an electrode carrier with the one or more bipolar electrodes thereon and having an open and a closed position, the method further comprising:
  positioning the RF applicator such that a distal tip of the RF applicator head in a closed position advances into the tubal ostium;
  deploying the RF applicator head into an open position such that the RF applicator head approximates the shape of the uterine cavity in a region of the tubal ostium; and
  passing current through the one or more bipolar electrodes to the tubal ostium to destroy the tissue to a known depth.

15. The method of claim 14, wherein passing current through the one or more bipolar electrodes to the tubal ostium to destroy tissue comprises vaporizing endometrium and destroying superficial myometrium.

16. The method of claim 14, further comprising:
  applying suction through the electrode carrier to draw surrounding tissue into contact with the electrodes and to draw moisture generated during ablation away from the electrodes to substantially prevent the formation of a low impedance liquid layer at the electrodes.

17. The method of claim 14, wherein passing current through the one or more bipolar electrodes comprises delivering radio frequency energy to the one or more bipolar electrodes.

18. The method of claim 14, further comprising:
  automatically terminating the flow of current into the tissue once ablation has approximately reached a predetermined depth of ablation.

19. The method of claim 14, further comprising:
  before positioning the RF applicator head at the tubal ostium, insufflating the uterine cavity; and
  before passing current through the one or more bipolar electrodes, ceasing insufflating the uterine cavity and allowing the uterine cavity to collapse onto the RF applicator head.

20. The method of claim 14, wherein the electrode carrier includes a fabric having conductive metallized regions and one or more non-conductive regions formed thereon to create the one or more bipolar electrodes.

21. The method of claim 8, further comprising:
  advancing an illuminator and an optical instrument into the uterine cavity; and
  wherein positioning the RF applicator head at the tubal ostium of a fallopian tube includes using the optical instrument to visualize the tubal ostium.

22. A method for fallopian tubal occlusion, comprising:
  transcervically inserting a tubal occlusion device through a uterine cavity and implanting the device into a fallopian tube where the tubal occlusion device occludes the fallopian tube;

transcervically inserting a substantially rigid, curved elongate member including a substantially cylindrically shaped electrode carrier positioned at a distal end with one or more bipolar electrodes formed thereon into the uterine cavity at a location proximal to the implanted tubal occlusion device such that the one or more bipolar electrodes are positioned proximally relative to the implanted tubal occlusion device;

positioning the electrode carrier at a tubal ostium of the fallopian tube such that a distal end of the electrode carrier advances into the tubal ostium; and passing radio frequency energy through the one or more bipolar electrodes to the tubal ostium to destroy tissue to a known depth and to precipitate a healing response in surrounding tissue that over time scars and occludes the fallopian tube;

wherein the tubal occlusion device remains in the fallopian tube after the elongate member is removed from the respective fallopian tube and provides immediate and at least temporary tubal occlusion before the scar tissue resulting from the application of current through the electrodes is formed.

23. The method of claim 22, wherein passing radio frequency energy through the one or more bipolar electrodes comprises:

passing a current at an initial current level through the one or more bipolar electrodes to the target tissue site to apply an initial power density to destroy tissue for an initial time period; and after the initial time period, ramping up the power density by increasing the current passed through the one or more bipolar electrodes to the target tissue site for a second time period.

24. The method of claim 23, wherein ramping up the power density comprises gradually increasing the current over the second time period.

25. The method of claim 23, wherein ramping up the power density comprises suddenly increasing the current from the initial current level to a second current level and applying the second current level for the second time period.

26. The method of claim 23, further comprising:

monitoring an impedance level at an interface between the electrode carrier and the tubal ostium;

where the initial time period is a time period after which a threshold decrease in the impedance level from an initial impedance level is detected.

27. The method of claim 23, where the initial time period is determined empirically as a time period after which an initial depth of tissue destruction has been achieved.

\* \* \* \* \*